US008363216B2

(12) United States Patent
Yuan et al.

(10) Patent No.: US 8,363,216 B2
(45) Date of Patent: Jan. 29, 2013

(54) CONTINUOUS MEASUREMENT OF AMINE LOADING IN GAS PROCESSING PLANTS USING RAMAN SPECTROSCOPY

(75) Inventors: Hongqi Yuan, Edmonton (CA); Allan Chambers, Edmonton (CA); John Woolley, Edmonton (CA)

(73) Assignee: Alberta Innovates—Technology Futures, Edmonton (CA)

( * ) Notice: Subject to any disclaimer, the term of this patent is extended or adjusted under 35 U.S.C. 154(b) by 251 days.

(21) Appl. No.: 12/411,130

(22) Filed: Mar. 25, 2009

(65) Prior Publication Data

US 2009/0244535 A1 Oct. 1, 2009

Related U.S. Application Data

(60) Provisional application No. 61/039,271, filed on Mar. 25, 2008.

(51) Int. Cl.
*G01J 3/44* (2006.01)

(52) U.S. Cl. ........................................ 356/301; 356/300

(58) Field of Classification Search .......... 356/300–334, 356/70, 73, 440, 436; 250/227.23, 573, 574
See application file for complete search history.

(56) References Cited

U.S. PATENT DOCUMENTS 6,100,975 A 8/2000 Smith et al.
6,774,992 B1 8/2004 Garver et al.

FOREIGN PATENT DOCUMENTS

| JP | 11258160 | 9/1999 |
|---|---|---|
| JP | H11-258160 | 9/1999 |

OTHER PUBLICATIONS

Process Instruments Inc., Website; Raman Scattering Technology; 12 pages.
Smith, Lee, et al.; Raman Spectroscopy Monitoring for Control of Rich and Lean Amine Streams; Gulf Coast Conference Abstract, Oct. 17, 2007.

*Primary Examiner* — Tri T Ton
(74) *Attorney, Agent, or Firm* — Geoffrey deKleine; Borden Ladner Gervais LLP

(57) ABSTRACT

The present invention provides a system and method for continuous measurement of acid gas concentration or amine loading in a basic solution using Raman spectroscopy.

17 Claims, 21 Drawing Sheets

CONTINUOUS MEASUREMENT OF AMINE LOADING IN GAS PROCESSING PLANTS USING RAMAN SPECTROSCOPY

CROSS REFERENCE TO RELATED APPLICATIONS

This application claims the priority benefit of U.S. Provisional Patent Application No. 61/039,271 filed Mar. 25, 2008 entitled "Continuous Measurement of Amine Loading in Gas Processing Plants Using Raman Spectroscopy", the contents of which are incorporated herein by reference.

FIELD OF THE INVENTION

The present invention relates to a system and method for continuous measurement of amine loading in gas processing plants using Raman spectroscopy.

BACKGROUND

In its natural state, "raw" or "sour" natural gas contains acid gases such as carbon dioxide ($CO_2$) and hydrogen sulphide ($H_2S$). The process to produce pipeline quality natural gas requires the removal of these naturally occurring gases, typically through a liquid absorption process. Conventional acid gas absorbing liquids commonly used in the industry include amine-based solutions, or liquid amine.

The chemical reactions between the amine solution and the acid gas are reversible, allowing for thermal regeneration of the "rich" amine solution to remove the $CO_2$ and $H_2S$. The regenerated "lean" amine solution is then reused for another acid gas absorption cycle. The thermal regeneration of the "rich" amine solution is the single most energy intensive step during the acid gas removal process.

Gas processing plants do not currently have a means of continuously measuring the acid gas concentrations in the loaded (rich) and the regenerated (lean) absorbing liquid. The acid gas ($CO_2$ and $H_2S$) loading of the absorbing liquid during the process is conventionally determined manually by a plant operator based on lab titration. In most cases, an excess amount of energy is used to regenerate the absorbing liquid in order to meet pipeline gas specifications. As a result, the absorbing liquid circulation rate and thermal regeneration temperatures are operated with a wide margin and are not optimized. The ability to measure the absorbing liquid acid concentration continuously, especially for the regenerated lean liquid, would be useful to the natural gas processing industry.

The inventors have identified that Raman spectroscopy can be used to measure the acid gas loading of the liquid absorption process. Raman spectroscopy is a spectroscopic method to study the chemical components in gas, liquid or solid state phases through the vibration or rotation of a molecule. Raman spectroscopy is commonly used to characterize chemical components by providing a fingerprint by which the molecule can be identified. Typically, a sample is illuminated with a light source in which the light is collected with a lens and sent through a monochromator. Wavelengths close to the laser line (due to elastic Rayleigh scattering) are filtered out and those in a certain spectral window away from the laser line are dispersed onto a detector. Spontaneous Raman scattering is typically very weak and, as a result, the main historical difficulty of employing Raman spectroscopy has been separating the weak inelastic ally scattered light from the intense Rayleigh scattered laser light. A Raman spectrometer consists of three main parts: a light source, a spectrograph and a detector.

The inventors are not aware of any previous application of Raman spectroscopy to the measurement of acid gases in a basic solution, such as an amine solution used in a gas processing plant.

SUMMARY OF THE INVENTION

The present invention relates to a system and method for continuous measurement of amine loading in gas processing plants using Raman spectroscopy.

In one aspect, the invention comprises a method of determining the concentration of an acid gas in a basic solution, comprising the steps of:
  (a) providing a sample of the basic solution, and obtaining a Raman spectrum having characteristic peaks;
  (b) comparing the sample Raman spectrum to a baseline or control Raman spectrum and determining a spectral change;
  (c) correlating the spectral change with the acid gas concentration.

The basic solution may be an amine solution or an alkaline salt solution. The spectral change may comprise an increase or decrease in a peak height, or area under a peak, or both. The spectral change may occur at a peak of about 2574 $cm^{-1}$. The spectral change may comprise a shift in a ratio of a first peak height or area to a second peak height or area. The first peak and second peak may be selected from the group consisting of:

| First ($cm^{-1}$) | Second ($cm^{-1}$) |
|---|---|
| 300 | 1280 |
| 280 | 200 |
| 900 | 1000 |
| 400 | 1000 |

In a second aspect, the invention may comprise a method of determining the concentration of an amine solution, comprising the steps of:
  (a) providing a sample of the amine solution, and obtaining a Raman spectrum having characteristic peaks;
  (b) comparing the sample Raman spectrum to a baseline or control Raman spectrum and determining a spectral change;
  (c) correlating the spectral change with the amine concentration.

In a third aspect, the invention may comprise a method of optimizing basic absorbent solution regeneration in a gas processing plant, comprising the steps of:
  (a) periodically sampling a lean stream basic solution or a rich stream basic solution, or both a lean stream and a rich stream;
  (b) obtaining a Raman spectrum from one or both of a lean stream basic solution or a rich stream basic solution;
  (c) comparing a spectral change in a measured Raman spectrum from a baseline or control Raman spectrum;
  (d) correlating the spectral change with an acid gas concentration, or basic solution loading, or both; and
  (e) if necessary, varying a regeneration parameter in response to the acid gas concentration or basic solution loading, or both.

The regeneration parameter may comprise an amine addition rate, or a heat addition rate.

In yet another aspect, the invention may comprise a system for optimizing basic absorbent solution regeneration in a gas processing plant, said system comprising:

(a) a sampler for periodically obtaining a sample of one or both of a lean stream basic solution or a rich stream basic solution;

(b) a Raman spectrometer to obtain a Raman spectrum from one or both of a lean stream basic solution or a rich stream basic solution;

(c) at least one memory, the memory containing a set of program instructions and at least one baseline or control Raman spectrum;

(d) at least one processor operatively connected to the memory, the at least one processor responsive to the program instructions to:

(i) compare a spectral change in the measured Raman spectrum from the baseline or control Raman spectrum;

(ii) correlate the spectral change with an acid gas concentration, or basic solution loading, or both; and (iii) determine if a change to a regeneration parameter is necessary, and if so, provide control information to implement the change.

In one embodiment, the system further includes an actuator, responsive to the control information, to change the regeneration parameter.

BRIEF DESCRIPTION OF THE DRAWINGS

The invention will now be described in relation to the drawings in which.

DETAILED DESCRIPTION OF PREFERRED EMBODIMENTS

Figure 1:
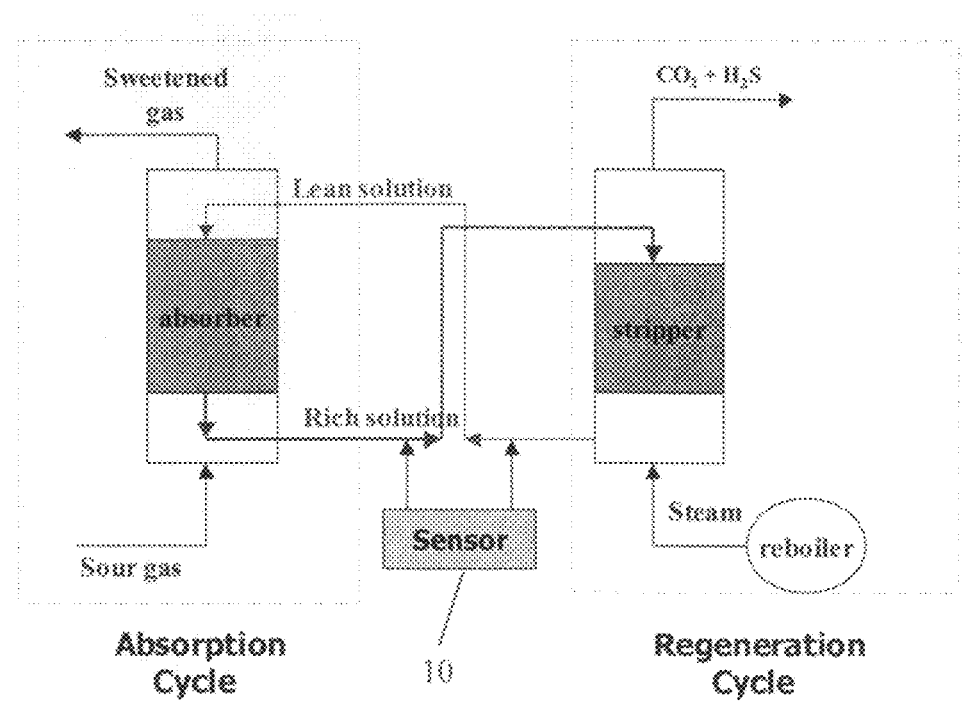
FIG. 1 is a schematic diagram of a conventional liquid amine absorption process.

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

The term "about" shall mean a range of values within plus/minus 10% of the stated value, or within the acceptable error range of methods or apparatuses used to measure the stated value. In particular, with respect to the peak shift of a Raman spectrograph, the term "about" indicates the inclusion of a peak value which differs slightly from the stated value because of differences in standardization, calibration or other factors unique to the measurement method or spectrometer.

Acid gases such as $CO_2$ and $H_2S$ and must be removed from a natural gas stream before its commercial sale. A liquid absorption process is commonly used for acid gas removal. The absorbing liquid chemically reacts with acid gases in an absorption cycle to produce a clean natural gas stream. The dirty absorbing liquid can be reused after a regeneration cycle, which cleans up the absorbing liquid.

In one aspect, the present invention comprises the use of Raman spectroscopy for online measurement of the chemical reaction and change in chemical components during acid gas absorption and regeneration. The inventors have developed a system and method using Raman spectroscopy to achieve continuous measurements of acid gas loading of absorbing solutions in liquid absorption processes commonly used in natural gas sweetening processes, such as aqueous amine based liquid absorption process. The most common acid gas components include $H_2S$ and $CO_2$. Possible other acid gas components can be measured simultaneously from the multi-streams; for example, the rich and lean amine acid loading can be measured at the same time. Using Raman spectroscopy to measure continuously $CO_2$ and $H_2S$ loading in the absorbing liquids from both absorption and regeneration cycle is not known in the gas processing industry. In addition, other unwanted chemicals produced during the processes can also be measured, such as heat stable salts and the chemicals from amine degradation and oxidation. The continuous online measurement can provide more frequent and accurate information for optimizing the process in gas processing plants.

Exemplary embodiments of the system and method of the present invention are described in the Examples, where laboratory measurements were obtained of some simulated samples using a process Raman spectrometer. These simulated samples comprise most commonly used absorbing solutions including monoethanolamine (MEA), diethanolamine (DEA), methyl diethanolamine (MDEA), diglycolamine (DGA), triethanolamine (TEA). diisopropanolamine (DIPA) and an inorganic based absorbing solution such as alkaline salt solutions, for example, potassium carbonate, sodium carbonate, sodium hydroxide, or potassium hydroxide. Other mixed amine/sulphur-based absorbing solutions, such as those involved in the Sulfinol™ process, can also be used. The inventors have found that Raman based spectroscopic measurement system and method may serve as a useful process control tool for gas processing plants.

As used herein, the term "basic solution" comprises a solution of an amine or an alkaline salt, including those absorbing solutions commonly used or known to absorb acid gases.

In current plant operations, utilizing amine absorption, amine circulation rates are determined through a manual measuring process with an approximate 12 hour frequency. In most cases, an excess amount of energy, typically 20-30% more steam than necessary is used to regenerate the amine as a safeguard in order to meet pipeline gas specifications. By utilizing the Raman spectroscopic based process monitoring system and method, which includes an interface to the gas process stream, continuous measurements of the acid loading (including both $H_2S$ and $CO_2$) from both rich amine and lean amine streams can be conducted simultaneously. The direct measurement of total acid loading in the rich and lean amine streams provide the process guide for the amine circulation rate and the steam (heat) flow rate for the regeneration cycle. Both amine circulation rate and steam flow rate are important and economically significant parameters. By optimizing one or both, significant cost savings may be achieved.

The Raman-based instrumentation system and method of the present invention may extend to other liquid absorption processes using other types of liquid absorbent basic solutions, such as alkaline salt solutions, for example, potassium carbonate, sodium carbonate, sodium hydroxide, potassium hydroxide solutions. In one embodiment, the system provides continuous measurement with result feedback to the process control, which preferably occurs in real-time. The system may be integrated into existing process streams.

Raman spectroscopy is a spectroscopic technique used in condensed matter physics and chemistry to study vibrational, rotational, and other low-frequency modes in a system. It relies on inelastic scattering, or Raman scattering of monochromatic light, usually from a laser in the visible, near infrared, or near ultraviolet range. The laser light interacts with phonons or other excitations in the system, resulting in the energy of the laser photons being shifted up or down. The shift in energy gives information about the phonon modes in the system. The basic principles of Raman spectroscopy as a general technique are well known in the art, and may be reviewed in Gardiner, D. J. (1989) Practical Raman spectroscopy, Springer-Verlag, ISBN 978-0387502540, the entire contents of which are incorporated herein by reference, where permitted.

In one embodiment, a system of the present invention may be integrated into an existing gas process stream, as schematically shown in FIG. 1. The sensor (10) may read one or both of the rich solution or the lean solution. In a preferred embodiment, multiple sampling of both the rich and lean solutions may take place. A multiple sampling analysis point is a set-up on a Raman spectrometer that could have multiple probes connected to the spectrometer and measure multiple streams from a process, such as, measuring the lean stream and the rich stream using one spectrometer.

Figure 2:
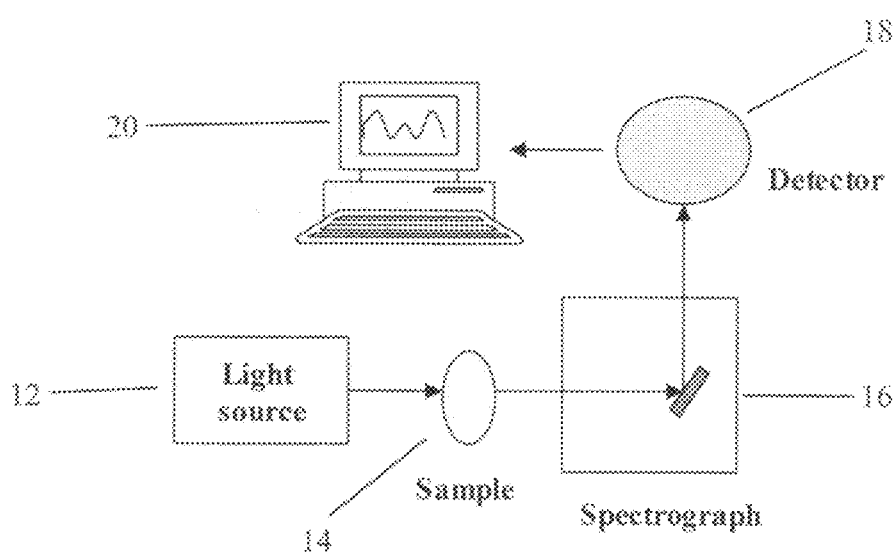
FIG. 2 is a schematic diagram of a Raman spectrometer.

As shown in FIG. 2, in one embodiment, the system comprises a light source (12) which passes through the sample (14) and which is then read in the spectrograph (16). The scattered light then passes to the detector (18) which reads the shifts in light energy, and passes that data onto a processor (20), which may be a general purpose computer running suitable software.

The information from a Raman spectrum is directly related to the chemical components in a liquid sample. Each different component will have a different functional group and will exhibit a different Raman spectrum. Different amines have their own characteristic Raman peaks. The intensity of each diagnostic Raman peak can be used to measure the concentration of the species in the solution. When the amine reacts with the $CO_2$ or $H_2S$, the Raman spectrum will be changed. The spectral change can be categorized as: 1) the spectral change of the amine itself, and 2) a spectral change related to the newly formed species. These spectral changes can then be used to measure the acid gas loading in the liquid amine phase.

The basic acid gas absorption reactions can be expressed using the following equations:

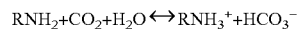

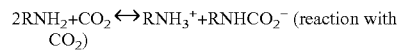

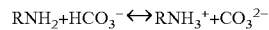

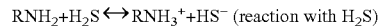

The free amine $RNH_2$ reacts with $CO_2$ or $H_2S$ to form ionized amine ($RNH_3^+$), carbamate ($RNHCO_2^-$), hydrogen carbonate ($HCO_3^-$), carbonate ($CO_3^{2-}$) and $HS^-$. These species have their own characteristic Raman peaks. The peak intensity also varies when the concentration of each species changes. By measuring these changes provided by Raman spectra, the concentration of $CO_2$ and $H_2S$ in rich amine and lean amine solutions can be measured.

Figure 4:
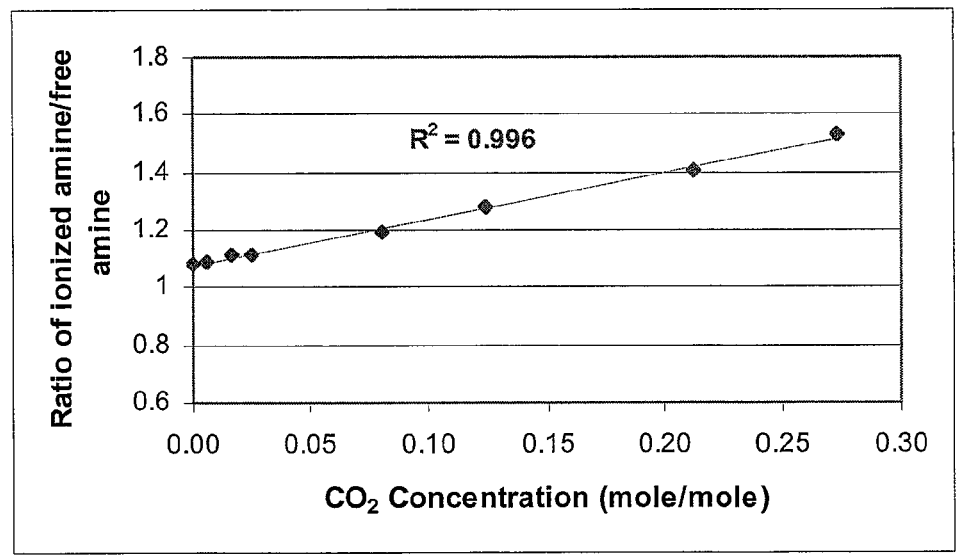
FIG. 4 is a graph showing the Raman peak ratio of ionized MDEA/free MDEA versus $CO_2$ concentration.
Figure 5:
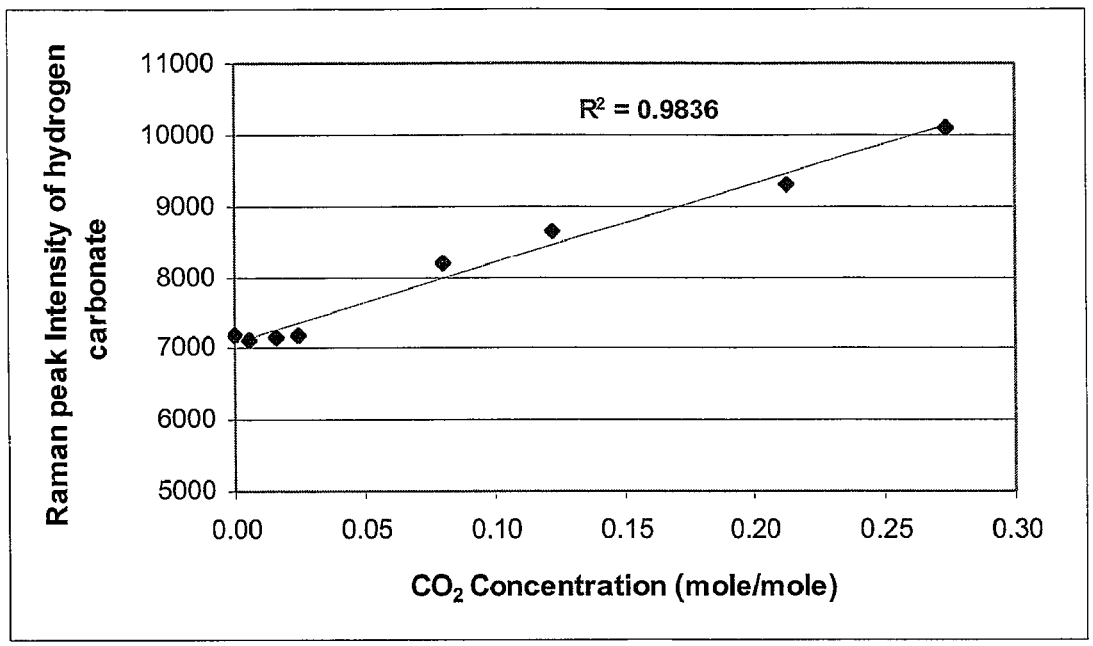
FIG. 5 is a graph showing hydrogen carbonate peak intensity versus $CO_2$ concentration in MDEA.
Figure 6:
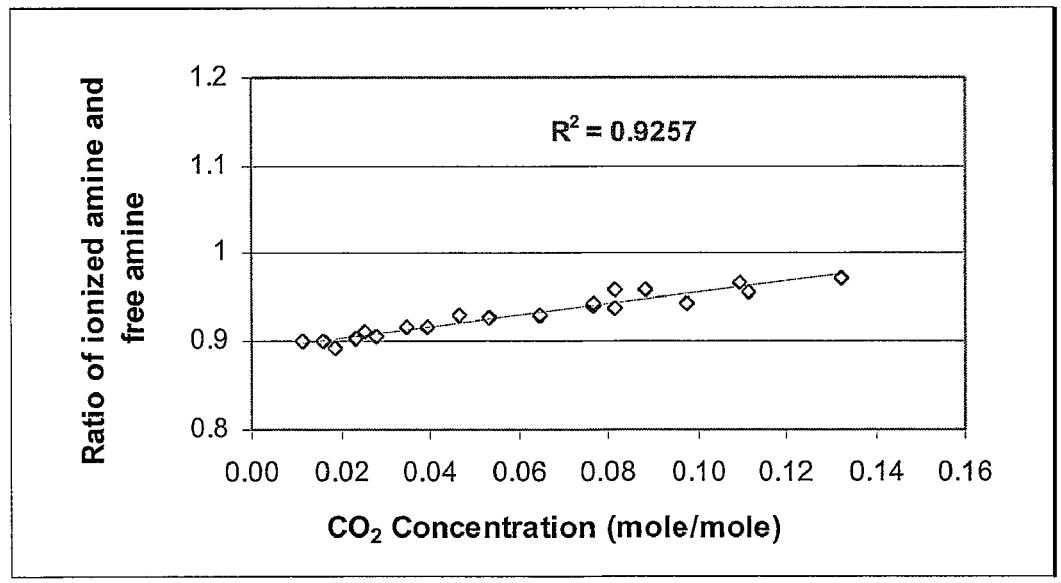
FIG. 6 is a graph showing the Raman peak ratio of ionized DEA/free DEA versus $CO_2$ concentration.
Figure 7:
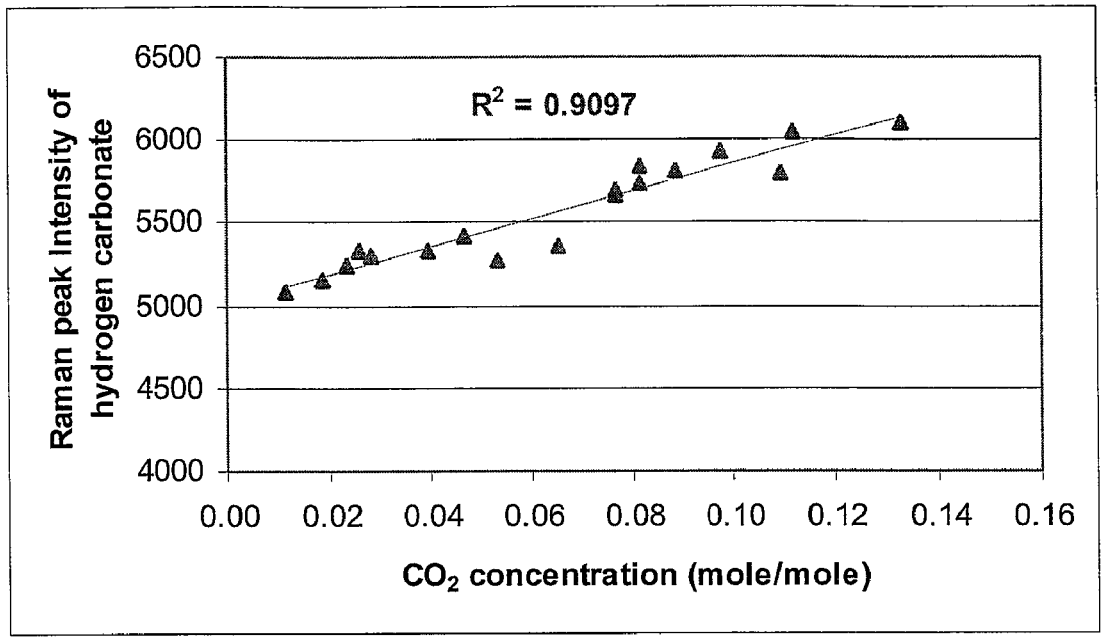
FIG. 7 is a graph showing hydrogen carbonate peak intensity versus $CO_2$ concentration in DEA.
Figure 8:
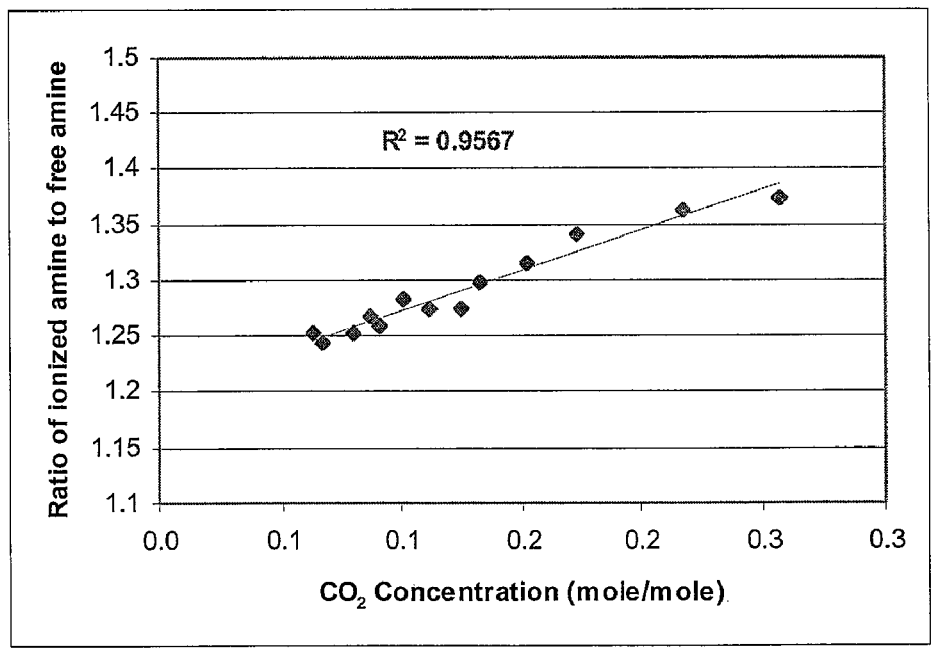
FIG. 8 is a graph showing the Raman peak ratio of ionized MEA/free MEA versus $CO_2$ concentration.
Figure 9:
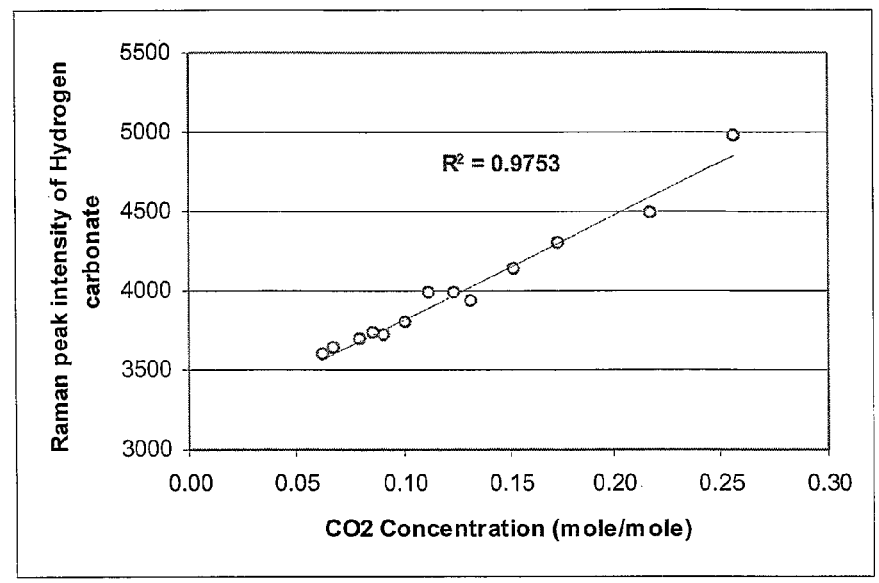
FIG. 9 is a graph showing the hydrogen carbonate peak intensity versus $CO_2$ concentration in MEA.
Figure 10:
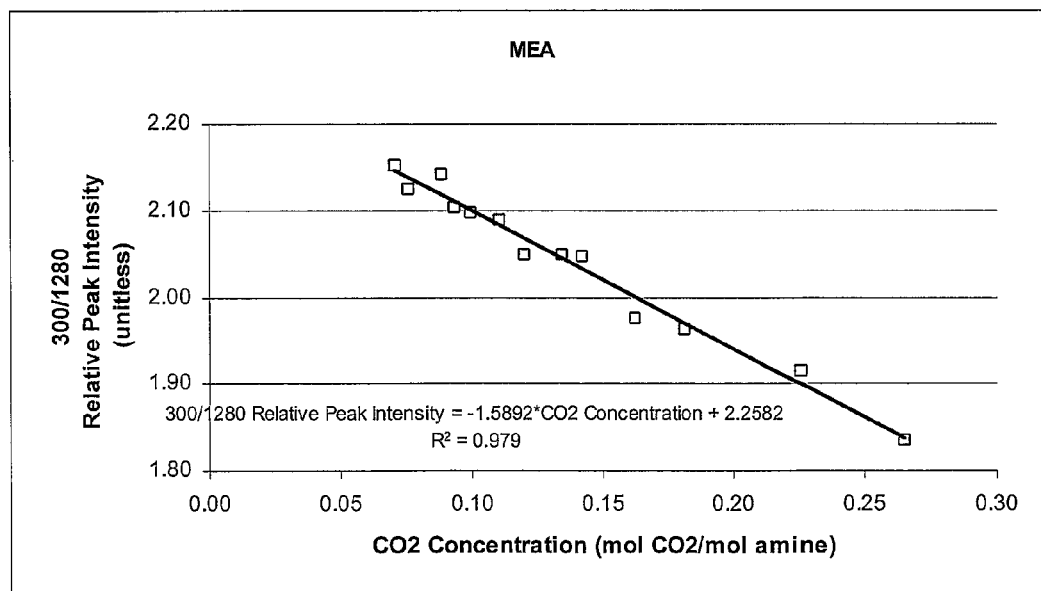
FIG. 10 is a graph showing MEA 300/1280 relative peak intensity correlation to $CO_2$ loading.
Figure 11:
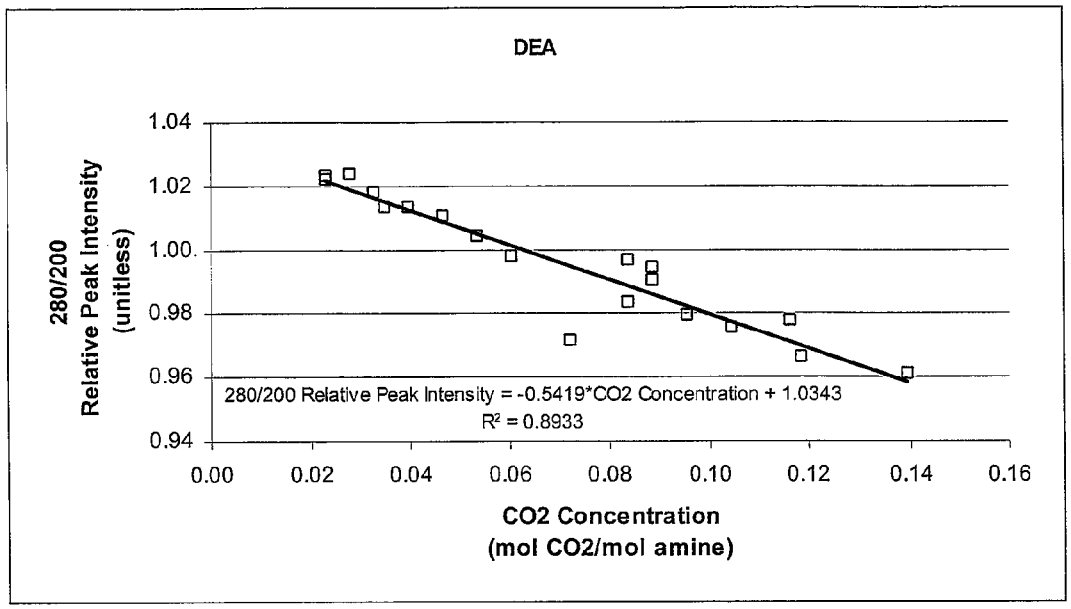
FIG. 11 is a graph showing DEA 280/200 relative peak intensity correlation to $CO_2$ loading.
Figure 12:
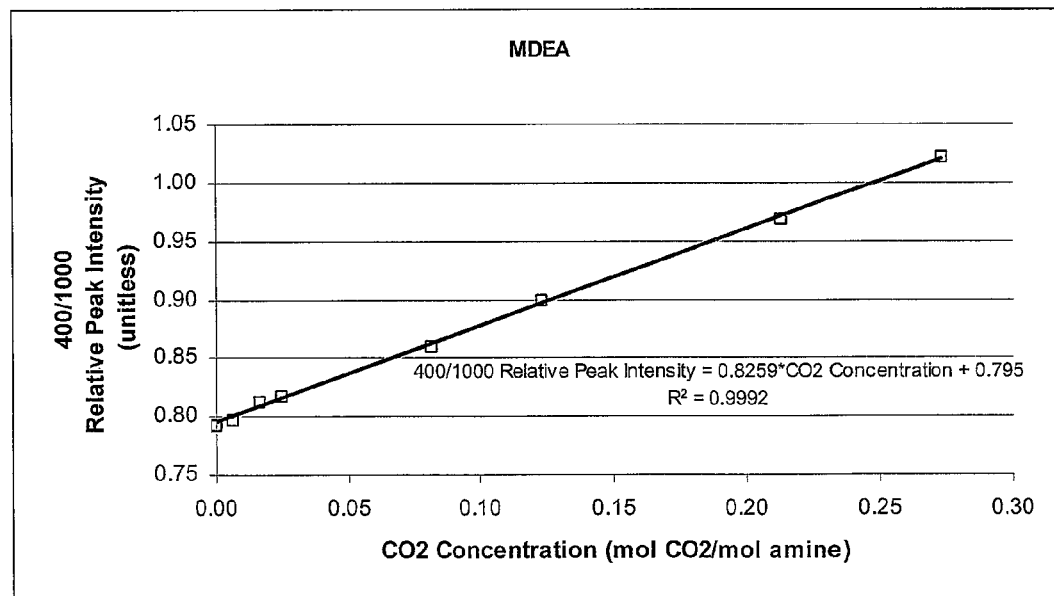
FIG. 12 is a graph showing MDEA 400/1000 relative peak intensity correlation to $CO_2$ loading.
Figure 13:
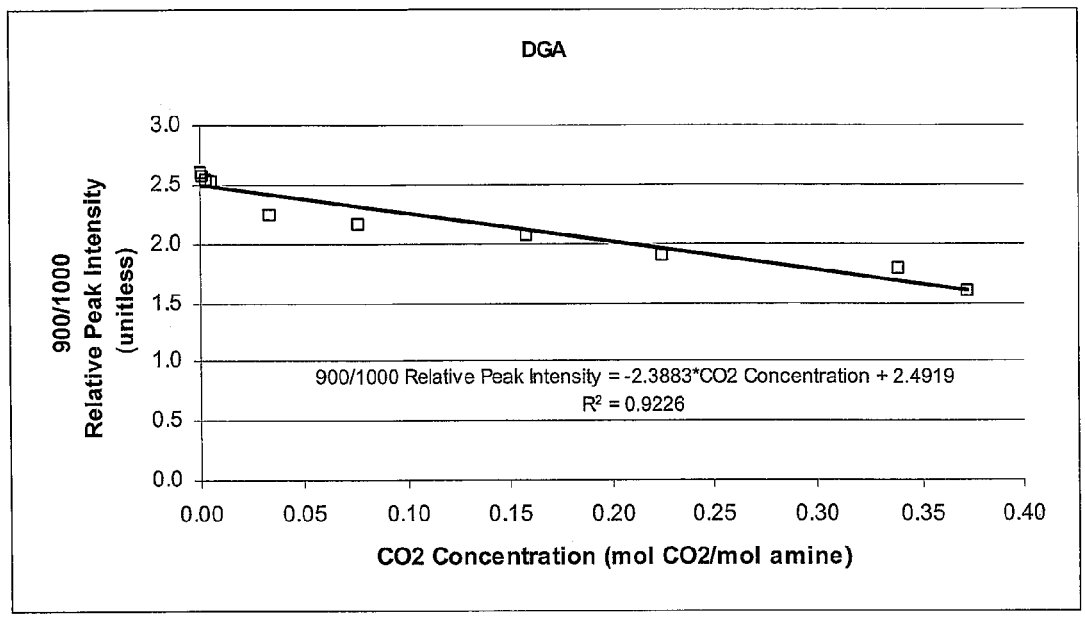
FIG. 13 is a graph showing DGA 900/1000 relative peak intensity correlation to $CO_2$ loading.

In one embodiment, peaks corresponding to ionized amine and free amine provide useful information. The inventors have found that the ratio of ionized amine to free amine correlates strongly to $CO_2$ concentration, as shown in FIGS. 4 and 6, and hydrogen carbonate concentration also correlates strongly to $CO_2$ concentration, as shown in FIGS. 5 and 7. In one embodiment, $CO_2$ concentration is measured as the molar ratio of $CO_2$ to amine.

In another embodiment, relative peak intensities may also be measured. The inventors have determined that the ratio of peaks of the Raman spectra is also indicative of acid gas concentration. For example, the ratio of peaks of about 300 $cm^{-1}$ and 1280 $cm^{-1}$ (within ±5 $cm^{-1}$ of these values) strongly correlates to $CO_2$ concentration in an MEA solution. Other useful peak ratios for different amines are provided below:

| | |
|---|---|
| MEA | 300 $cm^{-1}$/1280 $cm^{-1}$ |
| DEA | 280 $cm^{-1}$/200 $cm^{-1}$ |
| MDEA | 900 $cm^{-1}$/1000 $cm^{-1}$ |
| DGA | 400 $cm^{-1}$/1000 $cm^{-1}$ |

Figure 14:
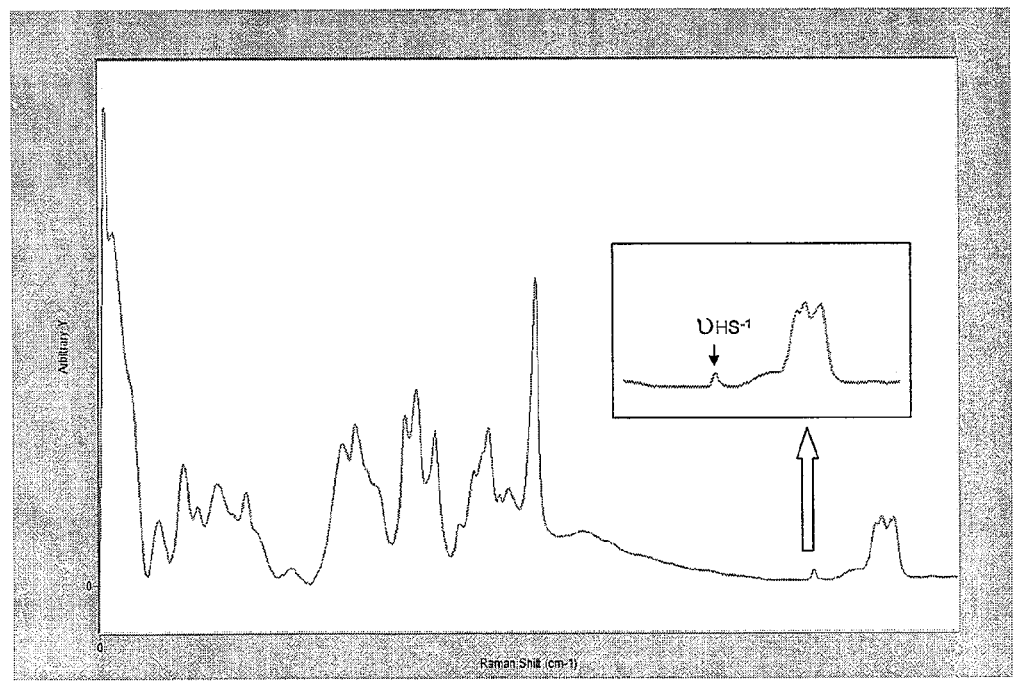
FIG. 14 shows the Raman spectrum of the DEA loaded with $H_2S$.

The typical Raman spectrum of DEA loaded with $H_2S$ is shown in FIG. 14. The inventors have determined that the peak at 2574 $cm^{-1}$ is related to the concentration of the $H_2S$ in the amine solution. Based on the peak area or intensity at 2574 $cm^{-1}$, the concentration loaded in the sample can be correlated with empirical chemical analysis results. In the alternative, or additionally, a ratio of the peak at 2574 $cm^{-1}$ to a baseline or normalized peak may be correlated with $H_2S$ concentration.

Elements of the present invention can be realized in hardware, software, or a combination of hardware and software. A typical combination of hardware and software could be a general purpose computer system or other data processing system with a computer program that, when being loaded and executed, controls the computer system such that it carries out the methods described herein. Program instructions includes any expression, in any language, code or notation, of a set of instructions intended to cause a data processing system having an information processing capability to perform a particular function either directly or after conversion to another language, code or notation, and/or reproduction in a different material form.

Figure 19:
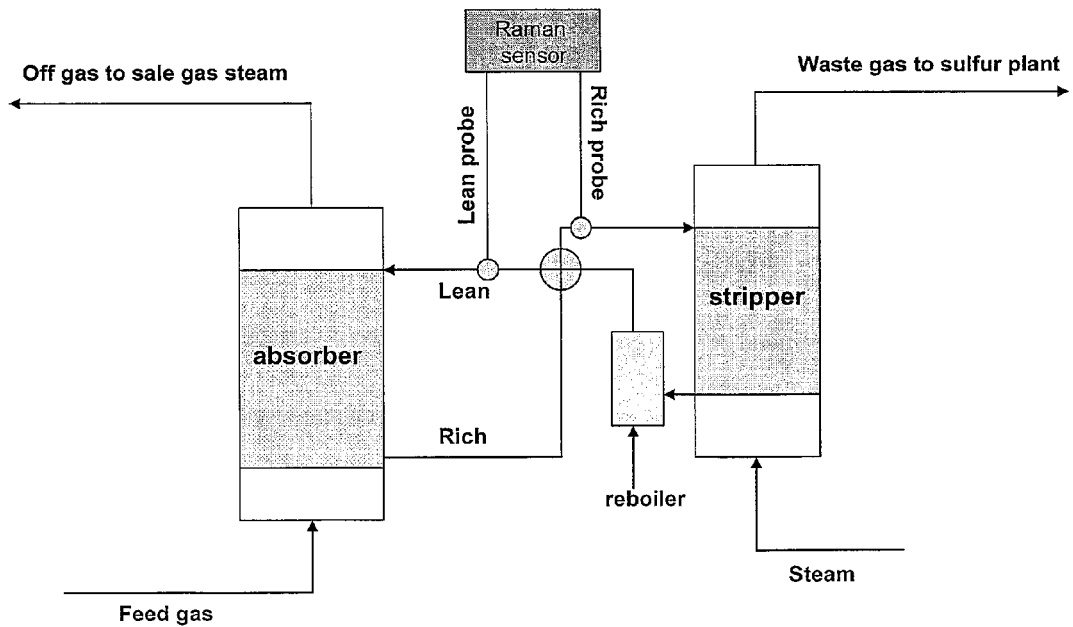
FIG. 19 is a schematic diagram of the Raman analyzer sampling location in the gas plant.
Figure 20:
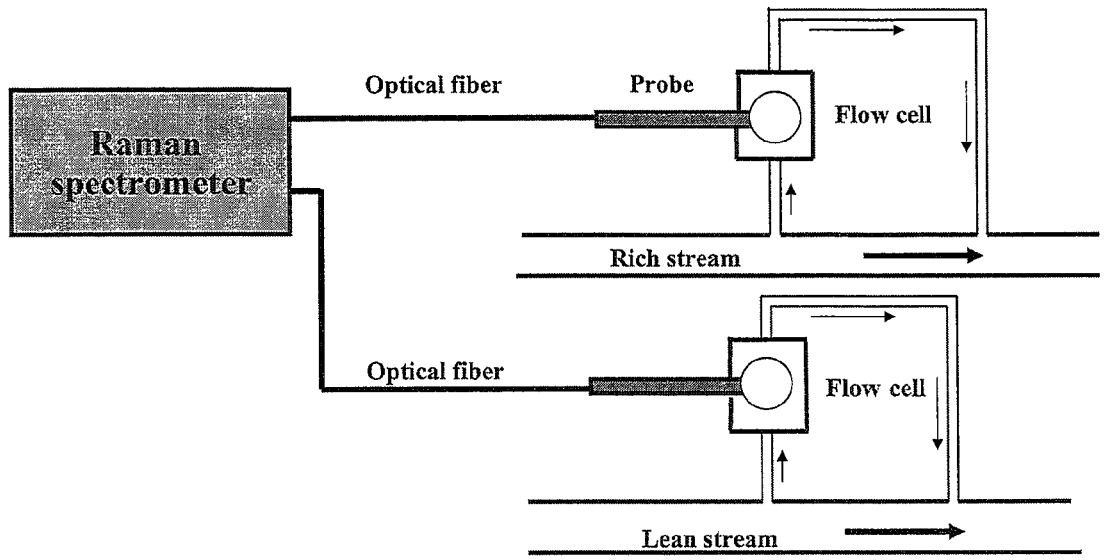
FIG. 20 is a schematic diagram of the Raman analyzer interface to plant process.

In one embodiment, the invention comprises a system for optimizing basic absorbent solution regeneration in a gas processing plant. Automatic or manual samplers are provided on each of the rich and lean amine streams, which are connected to a Raman spectroscopy system. The general configuration of such a system is schematically illustrated in FIGS. 19 and 20. The sampler may comprise a flow-through cell.

The system is conveniently implemented with a general purpose computer including conventional memory and a processor. The memory may contain a set of program instructions and at least one baseline or control Raman spectrum. The processor is responsive to program instructions which are coded to implement the method steps described herein.

In one embodiment, the program instructions cause the processor to (i) compare a spectral change in the measured Raman spectrum from the baseline or control Raman spectrum, (ii) correlate the spectral change with an acid gas concentration, or basic solution loading, or both, and determine if a change to a regeneration parameter is necessary, and if so, provide control information to implement the change.

The control information is then used to control at least one actuator to change the regeneration parameter. The actuator may be used to increase or decrease amine addition to the regeneration fluid, or the actuator may be used to increase or decrease the heat supplied in the regeneration process.

The present invention is described in the following Examples, which are set forth to aid in the understanding of the invention, and should not be construed to limit in any way the scope of the invention as defined in the claims which follow thereafter.

EXAMPLES

Example 1

$CO_2$ Loading Tests

This Example Involves the Comparison of a Chemical Analysis Method and a Raman Spectroscopy Measurement of the Same Sample Generated from the Absorption Reaction of $CO_2$.

Generation of Amine Samples with Different $CO_2$ Concentrations

To gather amine samples with varying concentrations of $CO_2$, a steady 0.18 Lpm stream of 15% $CO_2$ balanced with $N_2$ gas was bubbled through a ceramic sparger immersed in the amine solution. Samples of approximately 30 mL were then removed from the amine at specific time intervals, with a portion of each sample run through the Raman spectroscope and another portion being sent for titration. Samples with $CO_2$ sparging times between 10 minutes and 6 hours were taken to gather data for a wide range of $CO_2$ concentrations.

$CO_2$ Concentration Analysis from Titration

Titration was performed in accordance with UOP Method 829-82: Titrimetric Determination of $CO_2$ in Ethanolamines. This method prescribes a dilution of the amine sample in a standard volume of >99.8% purity methanol and to use sodium hydroxide (NaOH) as the titrant. Thymolpthaelin indicates when the titration is complete. Calculation of the $CO_2$ loading condition of the amine is performed according to the formula:

$$C = \frac{3.2(A - B)M}{V}$$

Where,

C, is the $CO_2$ concentration in the amine sample [scf $CO_2$/gallon amine]

A, is the volume of titrant needed for the amine sample [mL]

B, is the volume of titrant needed for the blank methanol solution [mL]

M, is the molarity of the NaOH solution [mol/L]

V, is the volume of amine sample used in the titration [mL]

Spectroscopic Measurement of the $CO_2$ Loading in Different Amines

Raman spectra of each acid gas loaded amine sample were collected from a Chromex™ R2000 Spectrometer. A diode laser with 785 m line and 125 mW power was used as the excitation source of the spectrometer. An ANDOR™ TE cooled CCD camera was used as the detector. The integration time of each spectrum was 30 seconds.

The Raman spectra of four different amine solutions (MEA, DEA, DGA and MDEA) with different $CO_2$ loading, were collected and spectral analysis of these spectra was conducted.

Figure 3:
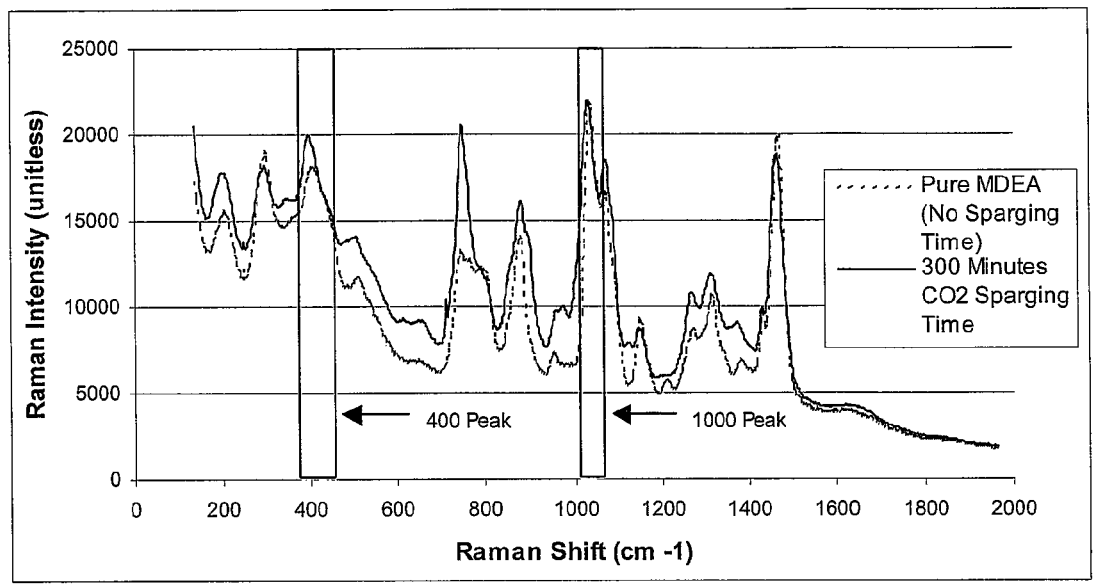
FIG. 3 shows MDEA Raman spectra for varying $CO_2$ sparging times.

Typical Raman spectra of pure MDEA and MDEA loaded with $CO_2$ are shown in FIG. 3. Comparing this set of spectra, it may be seen that there are significant spectral differences from the solutions of pure "unloaded" MDEA and the $CO_2$ loaded MDEA. These spectral differences can be used to label the amount of $CO_2$ in the amine solution.

After initial tests determined approximate loading conditions for a wide range of time intervals, the range was narrowed to include only those time intervals and concentrations wherein lean solution loading was normally experienced in gas processing plant operations [Engineering Data Book, Gas Processors Suppliers Association Vol. II, Sec. 21]. The ranges for each of the amine solutions are shown in Table 1:

TABLE 1

Amine Loading Ranges and Corresponding Sparging Times

| Amine | Normal Range-Lean Loading (mol $CO_2$/mol amine) | Corresponding Sparging Time (minutes) | Revised Experiment Range (minutes) | Sampling Period (minutes) |
|---|---|---|---|---|
| MEA | 0.12 | 90 | 60-120 | 5 |
| DEA | 0.08 | 45 | 20-60 | 2 |
| DGA | 0.10 | 150 | 100-200 | 10 |
| MDEA | 0.005-0.01 | ~9 | 4-9 | 1 |

Species Spectral Analysis

The use of a Raman spectra measurement used to determine the $CO_2$ loading in an amine solution was demonstrated by correlating peak intensity to $CO_2$ concentration obtained from the titration method.

The Raman peak assignments of three commonly used amines were given in Table 2.

TABLE 2

Raman band assignment of amines before and after acid gas absorption reaction

| | Raman peak cm$^{-1}$ | | |
|---|---|---|---|
| Species | MDEA | DEA | MEA |
| Ionized amine (RNH$_3^+$) | 745 | 787 | 867 |
| Free amine (RNH$_2$) | 792 | 820 | 839 |
| Carbamates (RNHCO$_2^-$) | 505 | 572 | 550 |
| Free amine (RNH$_2$) | 1465 | 1470 | 1467 |
| Hydrogen carbonate (HCO$_3^-$) | 1020 | 1020 | 1020 |
| Carbonate (CO$_3^{2-}$) | 1072 | 1072 | 1072 |

The correlation of $CO_2$ concentration and typical Raman peak measurements of MDEA are provided in FIGS. 4 and 5. As may be seen, there are close correlations between the ratio of ionized amine to free amine and Raman peak intensity of hydrogen carbonate and concentration of loaded $CO_2$.

The correlation of $CO_2$ concentration and typical Raman peak measurements of DEA and MEA are provided in FIGS. 6-9, where similar correlations may be seen.

Empirical Spectral Analysis

Table 3 shows the major peak relations for each of the samples investigated, and the correlation coefficient corresponding to the most linear peak ratios. Peaks entitled for example, "300" or "1280" peak, do not necessarily occur at exactly 300 cm$^{-1}$ or 1280 cm$^{-1}$, but are within ±5 cm$^{-1}$ of these values, and are thus titled for the sake of simplicity.

FIGS. 10-13 graphically illustrate the results from Table 3, and show the specific data points used to obtain the correlation coefficients shown.

TABLE 3

Amine Correlations Using Spectral Peak Ratios

| Amine | Concentration | Range Tested (mol $CO_2$/mol amine) | Peak Ratio Used for Correlation | Correlation Coefficient ($R^2$) |
|---|---|---|---|---|
| MEA | 19.4% | 0.06-0.26 | 300/1280 | 0.98 |
| DEA | 21.0% | 0.02-0.14 | 280/200 | 0.89 |
| DGA | 21.0% | 0-0.4 | 900/1000 | 0.92 |
| MDEA | 40.0% | 0-0.3* | 400/1000 | 0.999 |

*This range was used due to control restraints on taking several samples between the low and narrow range of 0.005 and 0.01 mol $CO_2$/mol amine, or between 4 and 9 minutes of $CO_2$ sparging time.

Example 2

$H_2S$ Loading Tests

This Example Involves the Comparison of a Chemical Analysis Method and a Raman Spectroscopy Measurement of the Same Sample Generated from the Absorption Reaction of $H_2S$.

Absorption Reaction Experiment

This experiment produced sample solutions with different concentrations of $H_2S$ absorbed in different aqueous amine solutions. The lab samples were generated by bubbling a gas stream of 2% $H_2S$ balanced with $N_2$ into an aqueous amine solution containing ~40% (v/v) of amine and ~60% (v/v) of water. The aqueous amine solution, which has the pH value ~12.70, absorbs the $H_2S$ into the amine solution. The off-gas, which is not absorbed by amine solution, is vented into a contained vent system for flaring at the certified $H_2S$ handling facility.

Samples of approximately 20 mL were then collected from the $H_2S$ loaded amine solution into closed sample containers for chemical and instrument analysis. The sample generation, chemical analysis, and Raman spectra analysis were conducted in the certified $H_2S$ handling facility at the Alberta Research Council (Edmonton, Canada).

Chemical analysis of $H_2S$ loading in the amine solution used the standard UOP Method 827-81. This method (providing control) and a precision method are used for determination of apparent hydrogen sulphide in amine solutions. Hydrogen sulphide is determined by oxidation with standard iodine solution in an acid medium. HCl is provided as the acidic medium. The chemical reaction is as follows:

$$H_2S + I_2(\text{excess amount}) ==== S + 2HI + I_2$$

According to the method, the amount of sample to be taken for analysis was determined from the following table and the precision method was selected for the sample analysis:

| Apparent $H_2S$ concentration expected in the sample (grains/gallon) | Sample Size mL |
|---|---|
| >100 | 1.0 |
| <100 | 5.0, 10.0 |

Sample Chemical Analysis Calculations

The concentration of apparent hydrogen sulphide in the sample solution was calculated as follows:

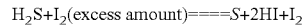

Apparent $H_2S$, grain/gallon = $1991(A \times M_1 - 0.5B \times M_2)/V$

Where,
 B, is the standard sodium thiosulfate solution [mL],
 $M_2$, is the molarity of the sodium thiosulfate solution [mol/L]

A, is the volume of titrant needed for the amine sample [mL]

$M_1$, is the molarity of the NaOH solution [mol/L]

V, is the volume of amine sample used in the titration [mL]

The apparent hydrogen sulphide concentration in grains/gallon may be converted to volumes of hydrogen sulphide, as a dry gas at 15.6 C (60 FO) and 101.3 kPa (760 mm) to volume of solution by dividing by 84.

The apparent hydrogen sulphide concentration my be converted to wt-ppm as follows:

Apparent $H_2S$, wt-ppm=17×C/S

Where,
C, is the apparent $H_2S$ content, grain/gallon
S, is the specific gravity of sample, 60/60° F. (15.6/15.6° C.)

The volume of standard iodine solution is varied with the hydrogen sulphide content of the amine solution sample. Sufficient iodine solution is taken so that about 10 mL of standard sodium thiosulfate solution are required for back titration. When the amine sample solution is concentrated and viscous, it is preferable to pipette the sample into an Erlenmeyer flask containing 50 mL of water. The pipette is rinsed with water into the flask. The diluted sample is then mixed with the acidified iodine solution. This procedure prevents the local neutralization of the iodine by strong amine solution. Since free amine reacts quite rapidly with iodine solution, the amine solution should contact iodine only in the presence of excess acid.

Raman Spectroscopic Measurement and Results Compared to the Chemical Analysis

Two sets of tests were conducted with two different types of Raman spectrometers. The first set demonstrates Raman measurement of $H_2S$ loading using the Chromex™ R2000 bench top Raman spectrometer. The amine solutions used in the first set were aqueous DEA and MDEA solutions. The samples loaded with different $H_2S$ concentration were collected and the Raman measurements and chemical analysis were conducted. The Raman spectra of each sample were acquired under following instrument conditions: 1) 785 nm was the laser line. 2) The power of the laser was 100 mW. 3) The integration time for each sample was 2 minutes. 4) The spectral range was from 100 to 3400 $cm^{-1}$.

The typical Raman spectrum of the DEA loaded with $H_2S$ is shown in FIG. 14. The peak at 2574 $cm^{-1}$ is the signature peak of $H_2S$ in DEA. The intensity of this peak is related to the concentration of the $H_2S$ in the amine solution. Based on the peak area or intensity at 2574 $cm^{-1}$, the concentration loaded in the sample can be correlated with the chemical analysis results.

Many other spectral changes occurred during the chemical reaction between amine and $H_2S$. These spectral changes could also be used to help quantify $H_2S$ load. Further details of spectral analysis are provided in Example 3.

Figure 15:
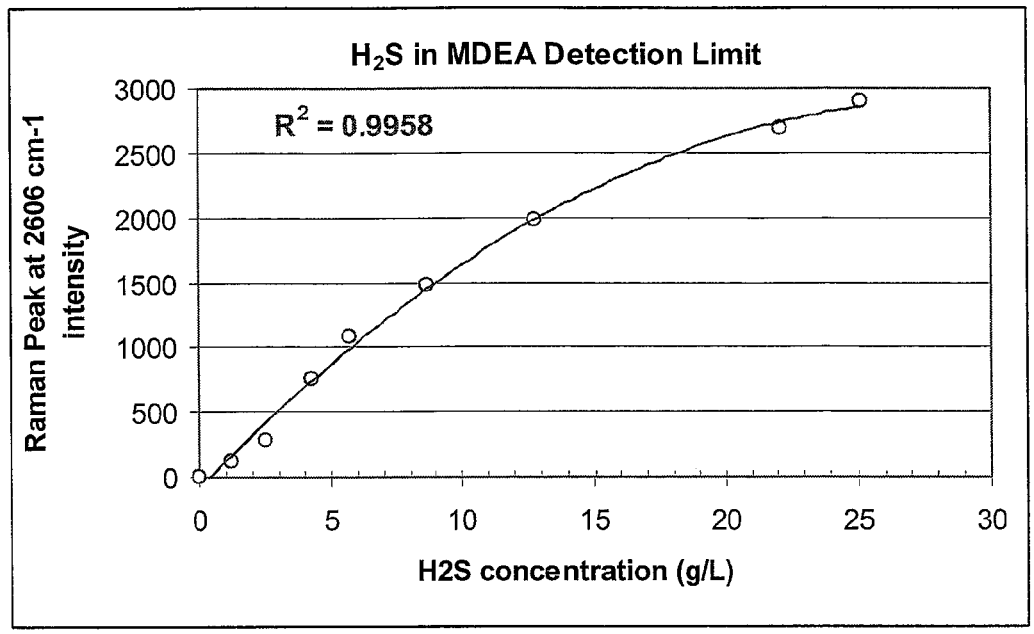
FIG. 15 is a graph showing the correlation of Raman peak at 2574 $cm^{-1}$ and $H_2S$ concentration.

The Raman spectra of MDEA with different $H_2S$ concentrations were collected and compared with the $H_2S$ concentration chemical analysis. The results were plotted as the correlation of the Raman $H_2S$ peak intensity (at 2606 $cm^{-1}$) and the $H_2S$ concentration (FIG. 15).

Figure 16:
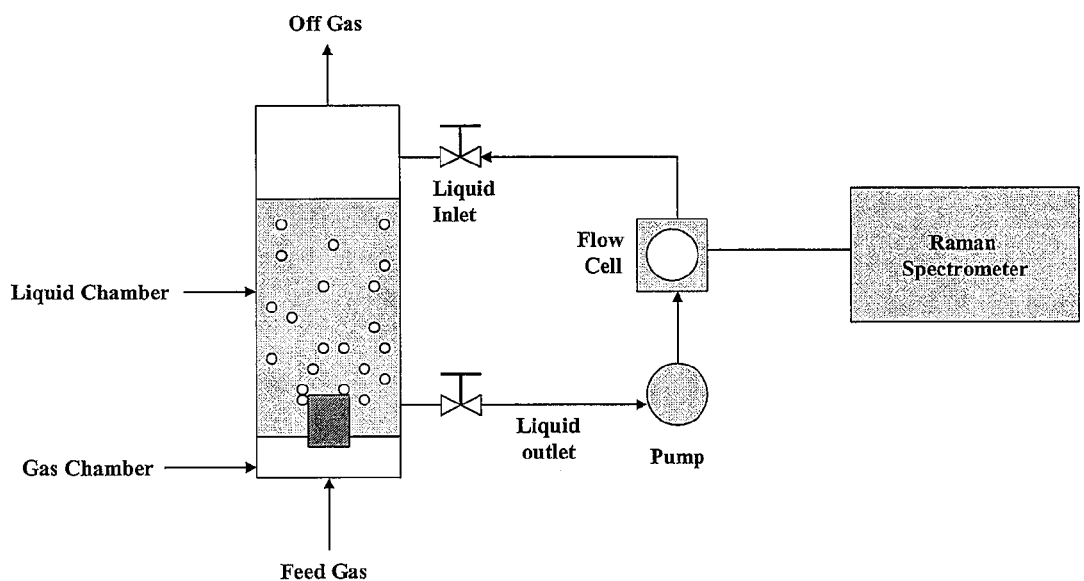
FIG. 16 is a schematic diagram of the simulated continuous measurement test set up.
Figure 18:
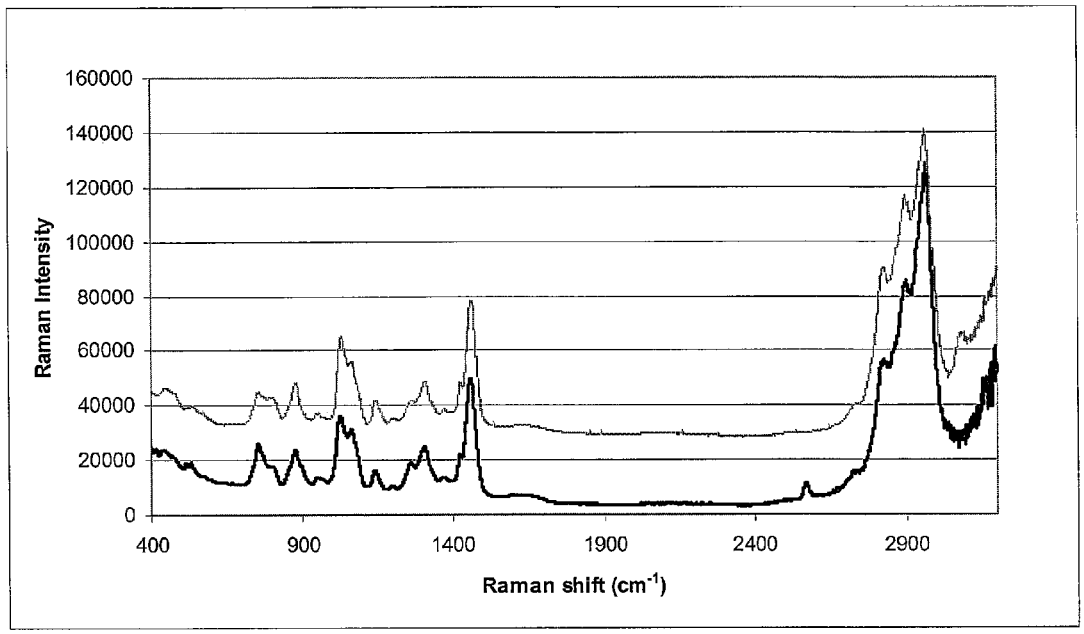
FIG. 18 shows the Raman spectra from the simulated continuous measurement.

A second set of Raman tests was conducted using the Bruker Sentinel™ R100 process Raman spectrometer and a custom made flow cell which was connected to the sample generation apparatus and simulated continuous measurement. The schematic diagram of the test set-up is shown in FIG. 16. A mixture of 750 mL 40% (v/v) MDE and 60% (v/v) water was filled in the sample generation chamber as the absorbing liquid. The liquid was pumped into the Raman flow cell and flowed back to the liquid chamber. The Raman spectrum was collected every 20 minutes through the Raman probe which is inserted into the flow cell while the 2% $H_2S$ gas flowed through the absorbing liquid. The test ran continuously for 4 days. The Raman spectra of the MDEA solution with different $H_2S$ loading were collected. The chemical analysis was conducted of the sample solution at the end of the test. The resulting spectra of this set of tests were plotted (FIG. 18). The dot line is the Raman spectrum obtained after just 10 minutes showing low levels of $CO_2$ or $H_2S$. The solid line in FIG. 18 is the Raman spectrum after 20 hours.

Example 3

Field Trial and Results

Figure 21:
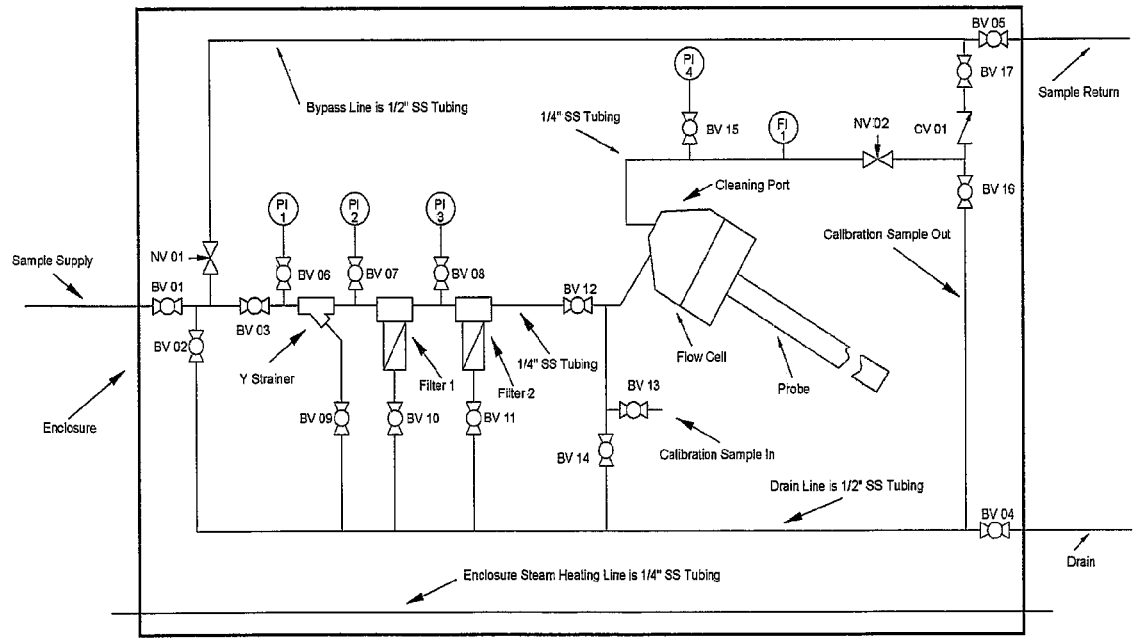
FIG. 21 is a design drawing of the sampling interface.

A field trial was conducted in a natural gas processing plant in Alberta. Two sample ports were connected to a measurement system of the present invention, as shown schematically in FIGS. 19 and 20. One port was from the rich amine stream after the heat exchange, before the stream entered the regeneration cycle. The second port is from the lean amine stream come out from the reboiler and after the heat exchange. The major components of measurement interface including the filtration system, flow cells, Raman probes and flow meter were enclosed in a box. The design of the sampling interface used is shown in FIG. 21. FIG. 21 gives the sampling interface including probe, flow cell and the three stage sample filtration system Between the interface and the Raman spectrometer, a 200 meter optic fiber cable was installed for optical signal transfer. The Raman signal of the sample flowing through the flow cell was collected by the optical probes and sent back to the spectrometer through the optical fiber cable. The Raman spectrometer controlled two probes and collected spectral data from the two probes every 20 minutes.

PC software was installed on the process Raman spectrometer computer. The on-line Raman measurement data was downloaded from the instrument computer to a remote location.

Figure 22:
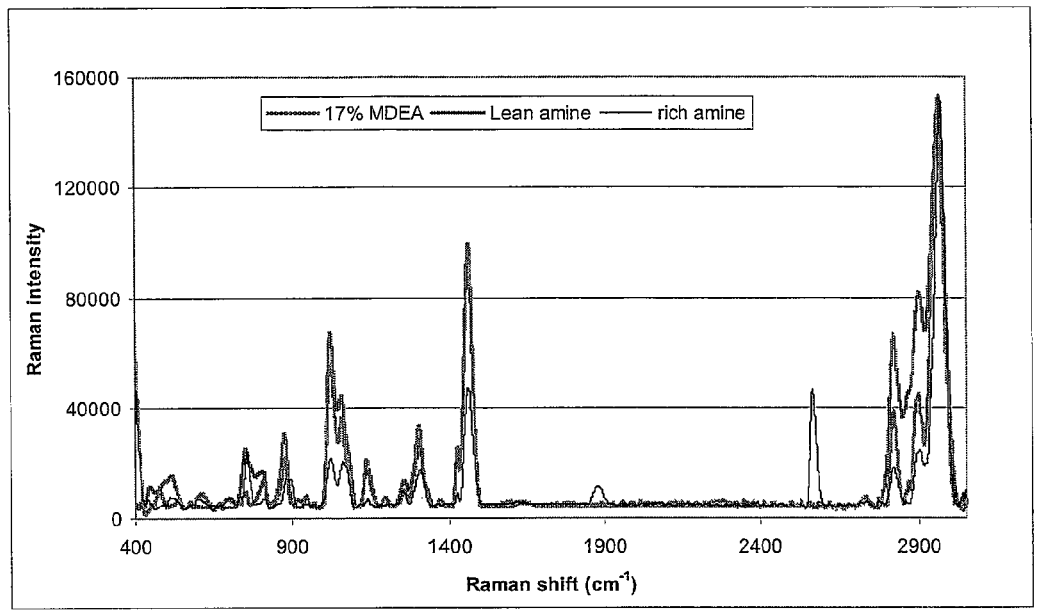
FIG. 22 shows a typical Raman spectra of pure MDEA, lean and rich amine solutions.

A five month period plant on-line measurement was conducted using the described set-up. The on-line Raman data were collected from both the rich and lean process streams. Typical Raman spectra of pure MDEA, lean and rich amine are shown in FIG. 22.

To be able to evaluate the on-line measurements, a comparison between the Raman measurements and the related plant process data is an important initial step. The key process data related to $H_2S$ loading, $CO_2$ loading and other data which indicated the process variation were provided by the gas plant. The collected on-line Raman data were processed using the following steps:

a) Convert original data file into XY data column (X: Raman shift with peak position, Y: Peak intensity).
b) Identify spectral component which related to the variation of the amine stream acid loading, including $CO_2$ and $H_2S$ loading, and the amine strength.
c) Conduct each signature peak calculation, on peak intensity or peak area (using suitable Spectrum Analysis Utilities™ software).
d) Plot the signature peak area against the time stamps results in the on-line raw data graphs.
e) Select one Raman peak for use as a reference peak ratio to the rest of the Raman peaks and generate the normalized on-line Raman results.

Figure 23:
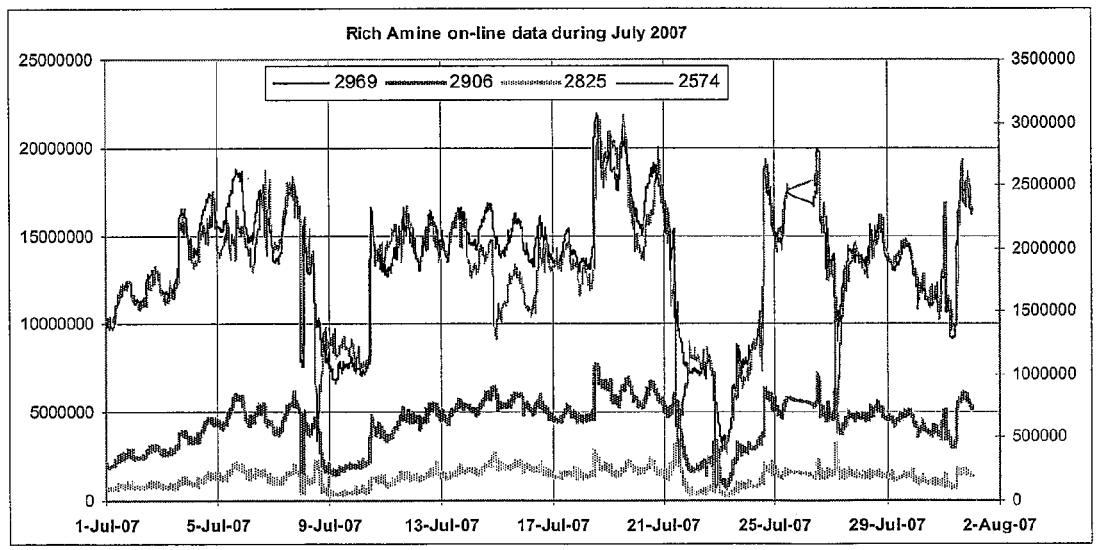
FIG. 23 is a graph showing Raman peak area versus time of four Raman peaks at 2969, 2906, 2825 and 2574 $cm^{-1}$ from rich probe.
Figure 24:
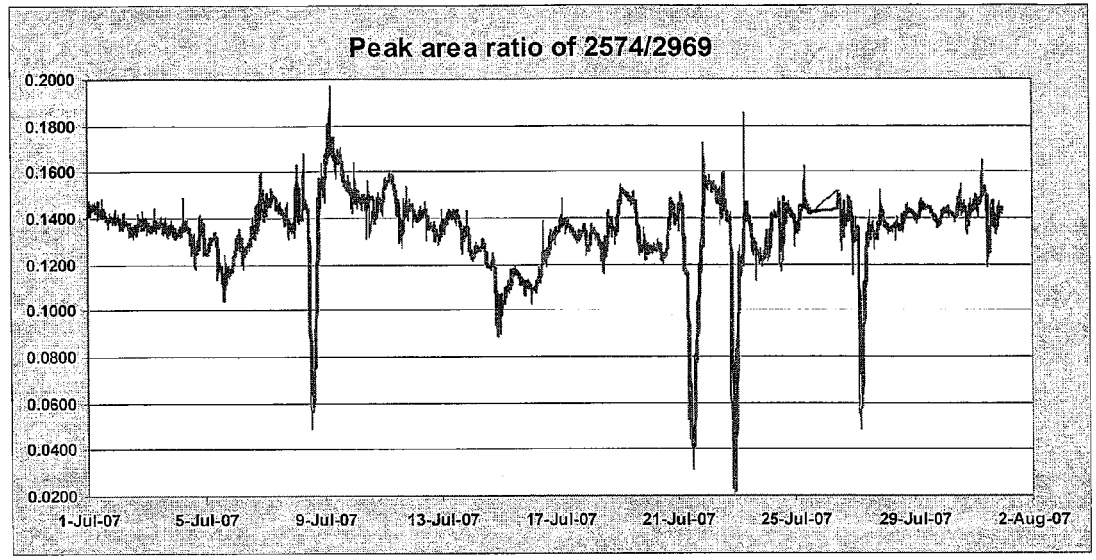
FIG. 24 is a graph showing a normalized Raman peak area of 2574 $cm^{-1}$ peak using Raman peak at 2969 $cm^{-1}$ as the reference peak.

A plot of Raman peak area versus time of four Raman peaks at 2969, 2906, 2825 and 2574 cm$^{-1}$ from rich probe is shown in FIG. 23. FIG. 24 is the plot of normalized Raman peak area of 2574 cm$^{-1}$ peak, using Raman peak at 2969 cm$^{-1}$ as the reference peak, versus time. The amine peak at 2969 cm$^{-1}$ was used as a reference due to its large peak area and low signal-to-noise ratio although any of the amine peaks can be used as reference.

The H$_2$S and CO$_2$ removal rate from the gas plant process is calculated based on the differences of H$_2$S and CO$_2$ levels in feed gas stream and the cleaned gas stream as follows:

H$_2$S removal rate(kg/hr)=Mass rate×(H$_2$Sin−H$_2$Sout)/1000000

Mass rate=calculated from absorber data
H$_2$Sin=H$_2$S level in combined inlet gas, ppm
H$_2$Sout=H$_2$S level in sweet gas from absorber, ppm CO$_2$ removal rate(kg/hr)=Mass rate×(CO$_2$in−CO$_2$out)/1000000

CO$_2$in=CO$_2$ level in combined inlet gas, ppm
CO$_2$out=CO$_2$ level in sweet sales gas, ppm The Raman peak at 2574 cm$^{-1}$ is characterized as the $v_{SH}$. This peak should strongly relate to H$_2$S loading in amine solution according to the overall basic chemical reaction:

R$_3$N+2H$_2$O+H$_2$S(g)+CO$_2$(g)-R$_3$NH$^+$+SH$^-$+2H$^+$+2HCO$_3^-$

Figure 25:
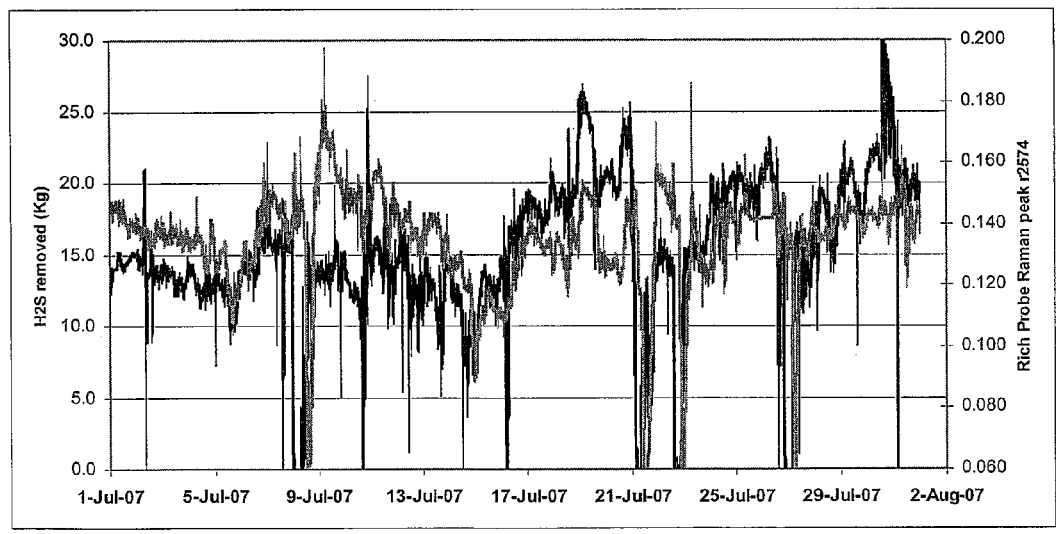
FIG. 25 is a graph showing the comparison of the calculated $H_2S$ removal rate (kg/hr) and the Raman peak ratio of 2574/2969 from rich probe (Black line—calculated $H_2S$ removal rate from the plant process data; Gray line—Raman peak ratio of 2574/2969).
Figure 26:
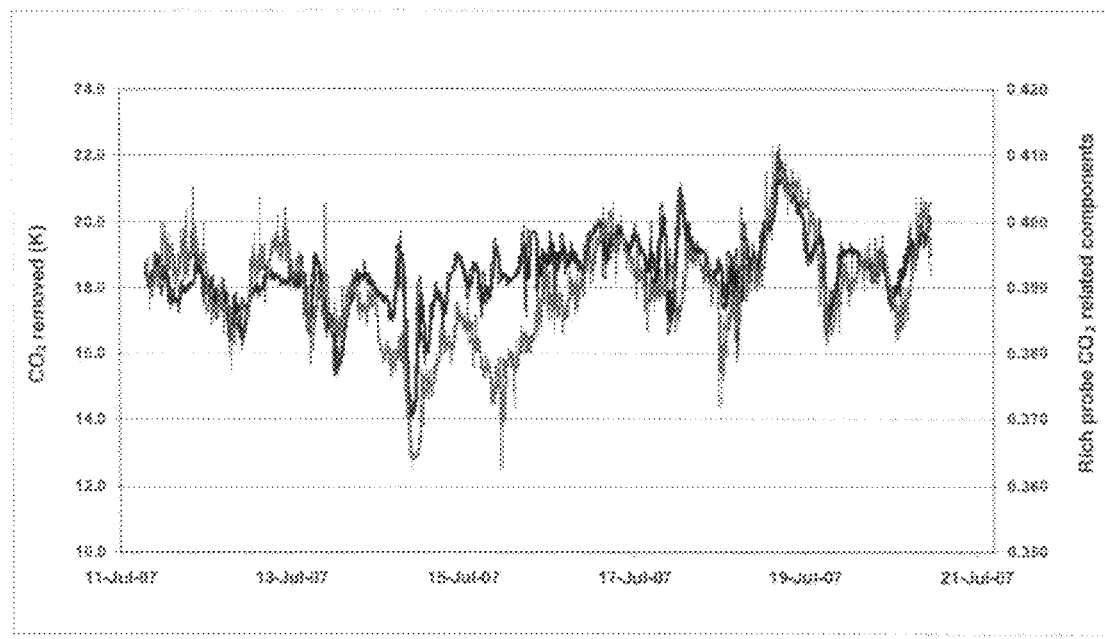
FIG. 26 is a graph showing the comparison of the calculated $CO_2$ removal rate (kg/hr) and the Raman peak ratio from rich probe (Black line—calculated $CO_2$ removal rate from the plant process; gray line—$CO_2$ loading related to Raman peak ratio).

The comparisons of the calculated H$_2$S and CO$_2$ removal rates from the plant process and the related Raman peak ratios are shown in FIGS. 25 and 26.

In FIG. 25, the black line is the calculated H$_2$S removal rate from the plant process data and the grey line is the Raman peak ratio of 2574/2969 cm$^{-1}$. This peak ratio is strongly related to the H$_2$S loading in amine solution, since the 2574 cm$^{-1}$ is the characteristic peak of the SH$^-$ in solution phase. Overall, the Raman data follows the plant process data, although there are also some periods that the Raman data is off the scale. A similar situation is shown in FIG. 26 for CO$_2$ comparison, in which a few Raman peak ratios were used as they relatively related to CO$_2$ loading in solution phase. The comparison results indicate that the Raman measurements overall follow the H$_2$S and CO$_2$ removal variation of the plant process. It shows that Raman spectral measurement provides strong indications of the acid gas loading including H$_2$S and CO$_2$ in amine solution in a continuous and non-invasive manner.

In a Raman spectrum for the spectral range of 3000 cm$^{-1}$ to 200 cm$^{-1}$, 18 Raman peaks in total were identified which related to H$_2$S and CO$_2$ loading in amine solution and also related to amine strength, i.e., the amine concentration in aqueous solution. The peak at 2969 cm$^{-1}$ was used as a reference peak and other peaks were normalized by ratio to peak 2969 cm$^{-1}$.

Principal Component Analysis (PCA) was conducted on all 17 normalized spectral peaks. For H$_2$S removal, top three ranked components and the percentage of variation they explain in the data sets are provided in Table 4. The most influential inputs in each component are shaded. Two data sets were created with the three components as inputs and the process data from gas plant as output. The data sets inputs and outputs are listed in Table 5.

TABLE 4

Principal Component Analysis for H$_2$S removal

| Cumm % | 51.93% | 77.34% | 90.67% |
|---|---|---|---|
| Percent_explained | 51.93% | 25.41% | 13.33% |
| Variances | 8.828 | 4.3201 | 2.2655 |
| Cumulative ranking | 2 | 3 | 1 |
| Components | 1 | 2 | 3 |
| Raman peak ratio* | | | |
| r2906 | 0.2611 | 0.282 | −0.1052 |
| r2825 | 0.1639 | 0.3275 | −0.3044 |
| r2574 | −0.0257 | −0.3308 | 0.4438 |
| r1885 | 0.3244 | −0.0722 | −0.0332 |
| r1467 | −0.2937 | 0.1799 | 0.1083 |
| r1424 | 0.0021 | 0.461 | 0.1167 |
| r1311 | −0.2292 | 0.2888 | 0.197 |
| r1263 | 0.2312 | 0.2228 | 0.33 |
| r1142 | −0.2515 | 0.2693 | −0.0464 |
| r1064 | −0.2527 | 0.2471 | 0.1818 |
| r1028 | −0.1769 | 0.3806 | 0.0692 |
| r881 | 0.0506 | −0.0254 | 0.6331 |
| r758 | 0.2889 | 0.0432 | 0.2689 |
| r644 | −0.2804 | −0.009 | 0.0569 |
| r452 | −0.2905 | −0.0162 | 0.0291 |
| r280 | 0.3216 | −0.1088 | −0.0691 |
| r217 | 0.3097 | −0.166 | −0.0561 |

*Raman peak at 2969 cm$^{-1}$ is used as the reference peak.

TABLE 5

Data sets for neural network prediction model for H$_2$S removal

| Data set 1 | | Data set 2 | |
|---|---|---|---|
| Inputs | Ouput | Inputs | Output |
| Component 1 | Feed gas H$_2$S, ppm | Component 1 | Sweet gas H$_2$S, ppm |
| Component 2 | | Component 2 | |
| Component 3 | | Component 3 | |

Figure 27:
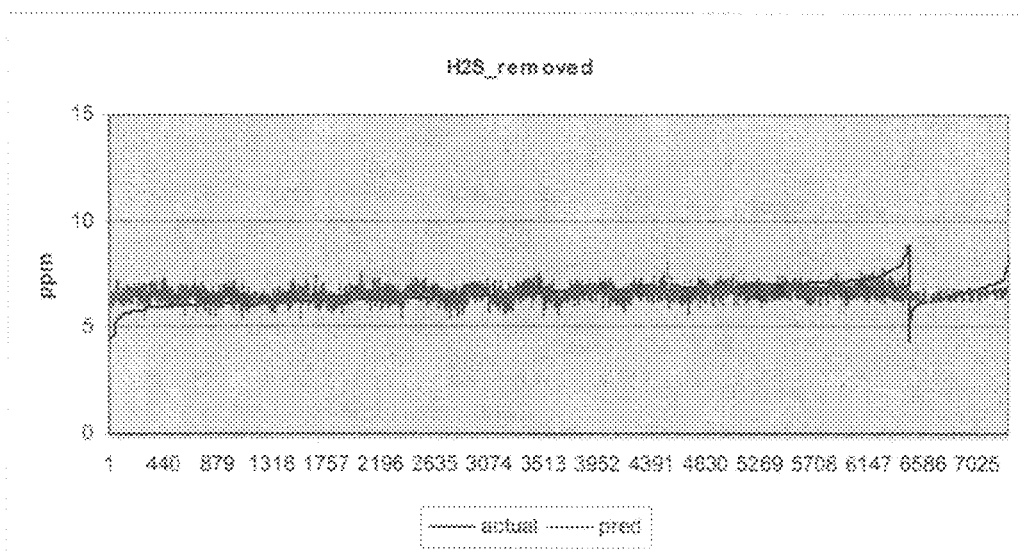
FIG. 27 is a graph showing the neural network prediction model test results for $H_2S$ removal.

A neural network (NN) prediction model was used to run the data sets. The results were plotted (FIG. 27), and indicated that the PCA components can be considered to be fairly good predictors of H$_2$S$_{in}$ and H$_2$S$_{removed}$. Attributes (components) were ranked based on their weighted effect in the NN. Cumulative ranking is indicated in Table 4. Component 3 was ranked most influential on H$_2$S. The largest coefficients of Component 3 (i.e., most influential inputs) are r2574 and r881.

The PCA analysis was also conducted for the CO$_2$ removal and top three ranked components and the percentage of variation in the datasets were also given in Table 6. The most influential inputs in each component are shaded.

TABLE 6

Principal Component Analysis for CO₂ removal

| | | | |
|---|---|---|---|
| Cumm % | 51.94% | 77.37% | 90.64% |
| Percent_explained | 51.94% | 25.43% | 13.27% |
| Variances | 8.8304 | 4.323 | 2.2554 |
| Cumulative ranking | 2 | 1 | 3 |
| Components | 1 | 2 | 3 |
| Raman peak ratio* | | | |
| r2906 | 0.2606 | 0.283 | -0.1041 |
| r2825 | 0.1636 | 0.3292 | -0.3017 |
| r2574 | -0.0252 | 0.3321 | 0.4431 |
| r1885 | 0.3243 | -0.0722 | -0.0319 |
| r1467 | -0.2942 | 0.1781 | 0.1068 |
| r1424 | 0.001 | 0.4608 | 0.119 |
| r1311 | -0.2297 | 0.2881 | 0.1966 |
| r1263 | 0.2312 | 0.2228 | 0.3307 |
| r1142 | -0.2516 | 0.2692 | -0.0435 |
| r1064 | -0.2536 | 0.2454 | 0.1796 |
| r1028 | -0.1776 | 0.3796 | 0.0689 |
| r881 | 0.051 | -0.0268 | 0.6344 |
| r758 | 0.289 | 0.0437 | 0.2699 |
| r644 | -0.2795 | -0.0077 | 0.0612 |
| r452 | -0.2903 | -0.0155 | 0.0316 |
| r280 | 0.3215 | -0.1092 | -0.0699 |
| r217 | 0.3095 | -0.1666 | -0.0568 |

TABLE 7

Data sets for neural network prediction model for CO₂ removal

| Data set 1 | | Data set 2 | |
|---|---|---|---|
| inputs | output | inputs | output |
| Component 1 | Feed gas CO₂, ppm | Component 1 | Sale gas CO₂, ppm |
| Component 2 | | Component 2 | |
| Component 3 | | Component 3 | |

Figure 28:
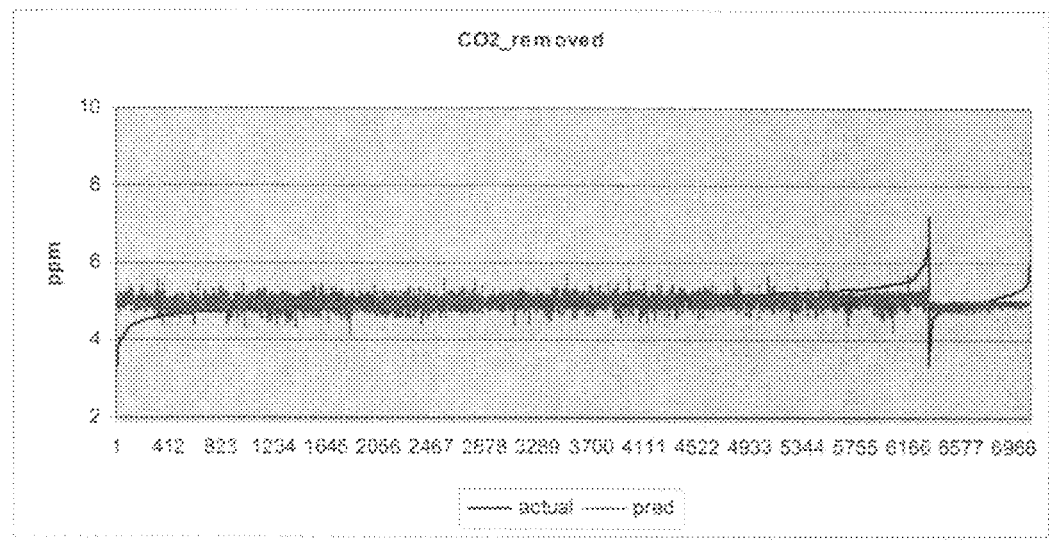
FIG. 28 is a graph showing the neural network prediction model test results for $CO_2$ removal.

The neural network (NN) prediction model on the datasets and the results were plotted (FIG. 28). The components were ranked based on their weighted effect in the NN. Cumulative ranking was provided in Table 6. Component 2 was ranked most influential on CO₂. For CO₂ removal, the largest coefficients of Component 2 (i.e. most influential inputs) are r1424, r1028, r2574 and r2825.

Example 4

Amine Strength Measurement Using Raman Spectra

To be able to determine the amine solution concentration or amine strength is an important factor for plant processing. If the amine solution is not strong enough, the efficiency of removal of the acid component from the sour gas would not be satisfied. Knowing the strength of the clean amine before it enters the absorber becomes a very important issue. The Raman spectra signal can be used to determine the amine strength because a Raman spectrum of an aqueous solution provides not only information regarding the chemical component in the solution, but also a water peak which is at 1640 cm$^{-1}$. The ratio of amine peak to water peak can be used to calculate the amine strength of the aqueous amine solution.

Figure 29:
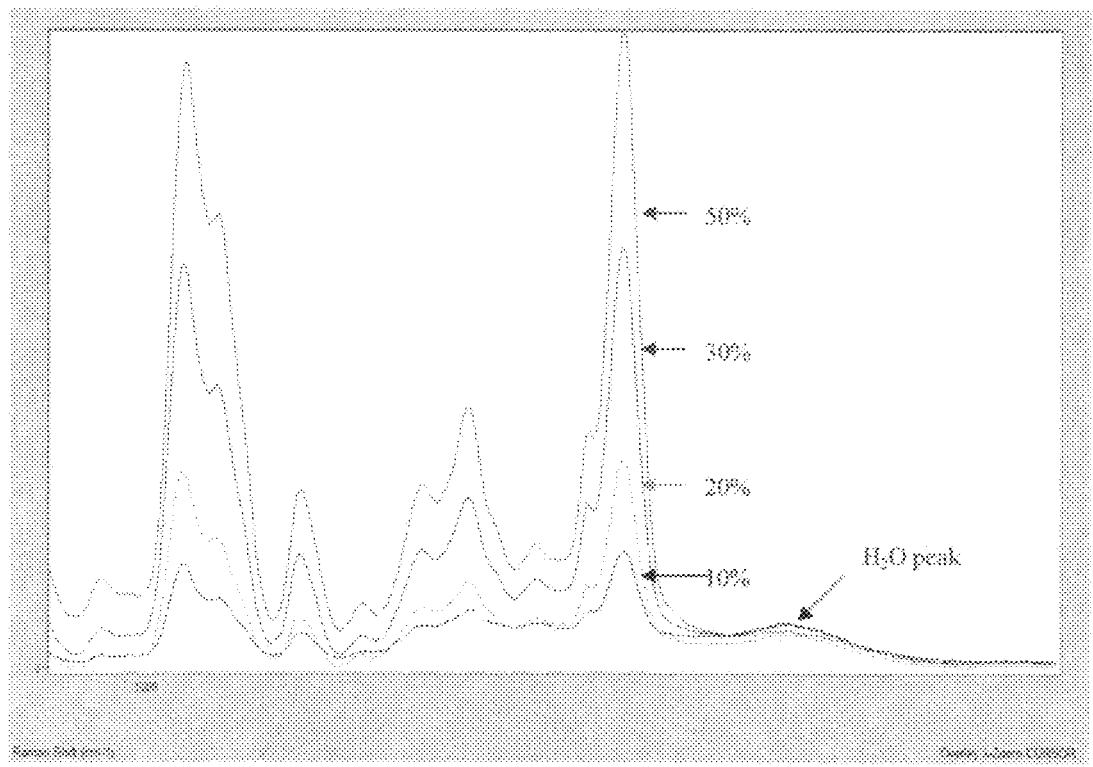
FIG. 29 shows the Raman spectra of MDEA solutions with different concentration.

A set of aqueous amine solutions was made with MDEA and water. The weight % of MDEA in the solution was 10, 20, 30, 40, 50, 60, 70, 80, and 90%. The Raman spectra of these solutions were collected. FIG. 29 provides a few spectra with different MDEA concentration. With increase of the amine strength, the amine peak intensity increases significantly, while the water peak intensity decreases with the amine strength increase but not significantly. The ratio of the amine peak intensity to the water peak intensity (i.e., amine strength) can be determined.

Figure 30:
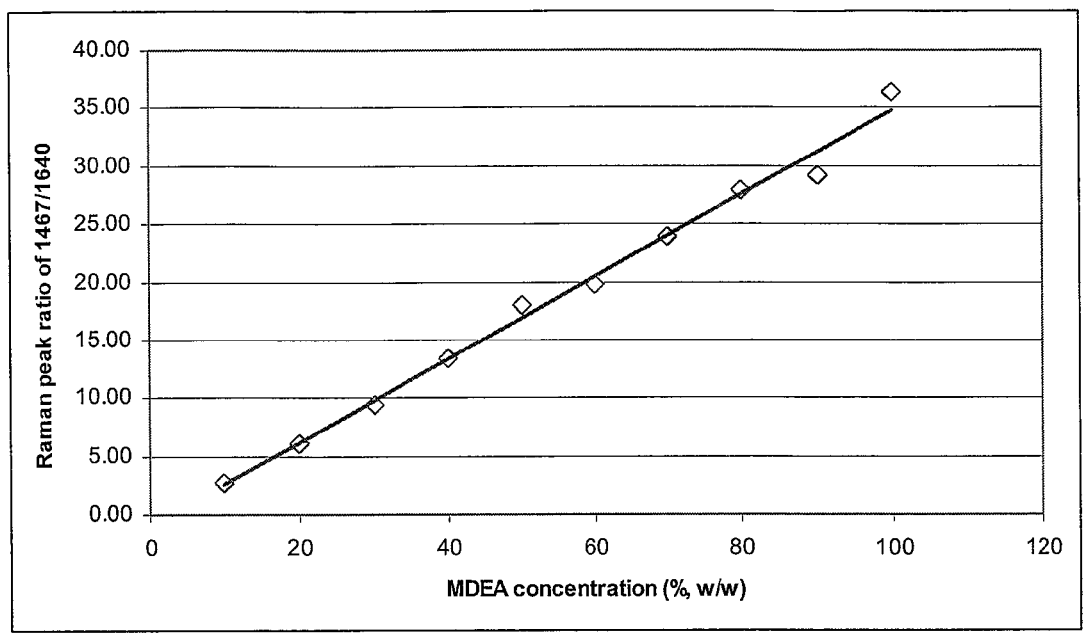
FIG. 30 is a graph showing the MDEA concentration vs. the Raman peak intensity ratio $1467_{(MDEA)}/1640_{(water)}$.

The MDEA concentration versus the Raman peak intensity ratio $1467_{(MDEA)}/1640_{(water)}$ were plotted (FIG. 30). The Raman peak ratio 1467/1640 has excellent linear correlation to the MDEA solution concentration.

Other MDEA peaks including 2906 cm$^{-1}$, 2825 cm$^{-1}$, 1131 cm$^{-1}$, 1263 cm$^{-1}$ etc. could also be used to determine the amine strength.

Figure 31:
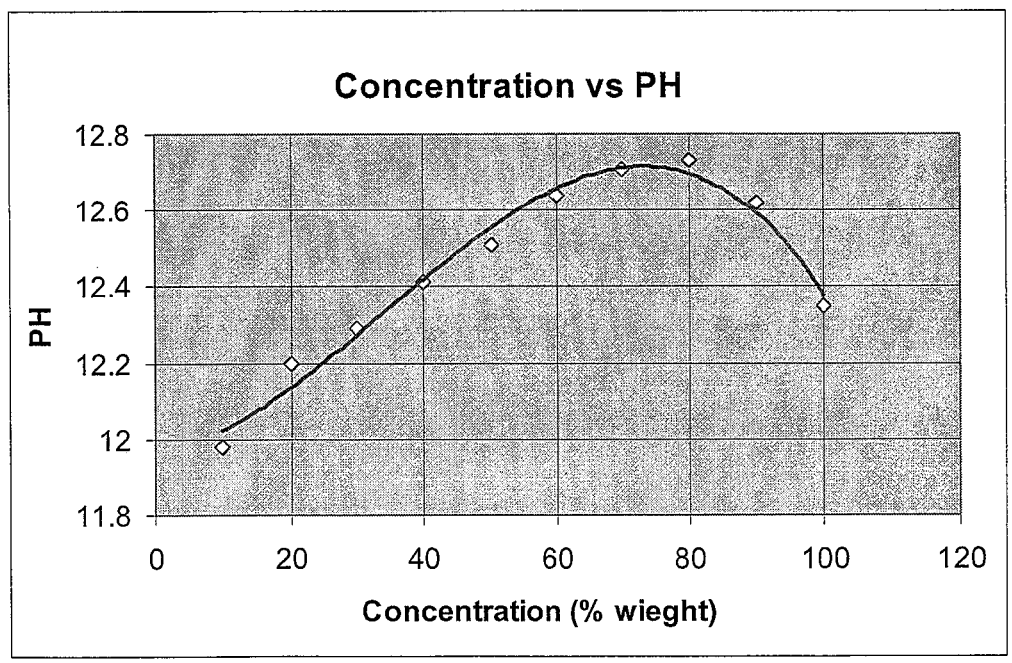
FIG. 31 is a graph showing the correlation of pH value and the MDEA solution concentration.

The pH value of the MDEA at different concentration was also measured and the correlation of the pH value and the solution concentration was plotted (FIG. 31).

Example 5

Determination of the Acid Loading of Other Inorganic Based Absorbing Solution

Figure 32:
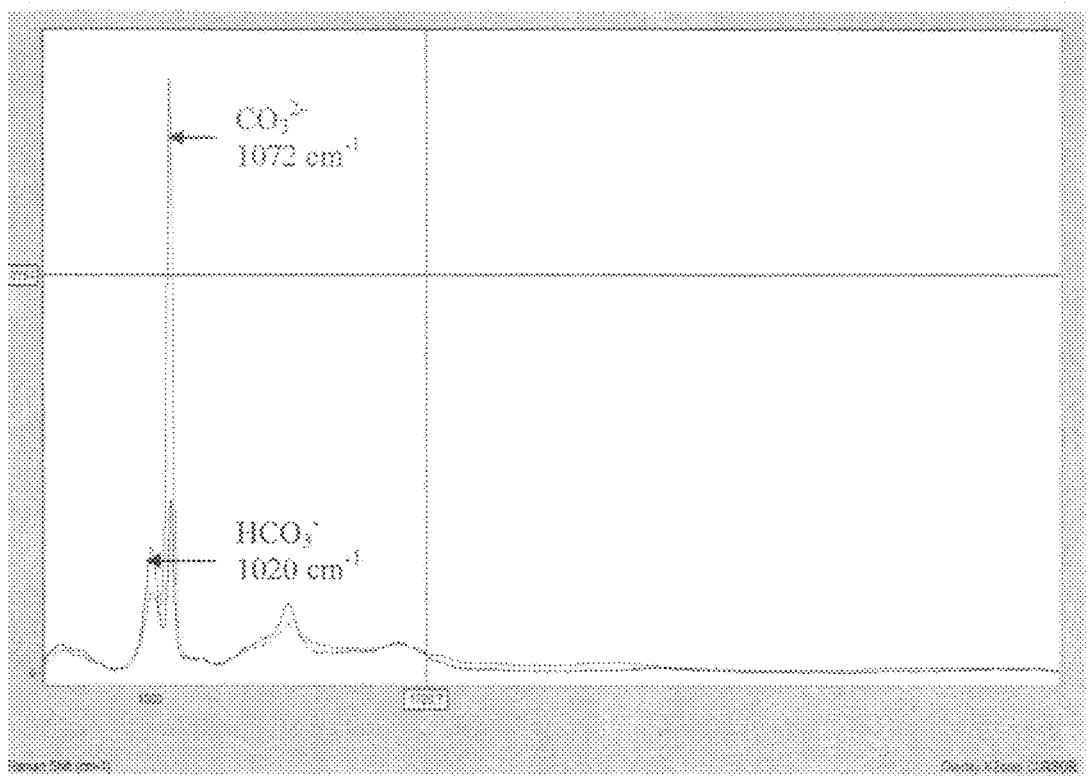
FIG. 32 shows the Raman spectra of carbonate and bicarbonate.
Figure 33A:
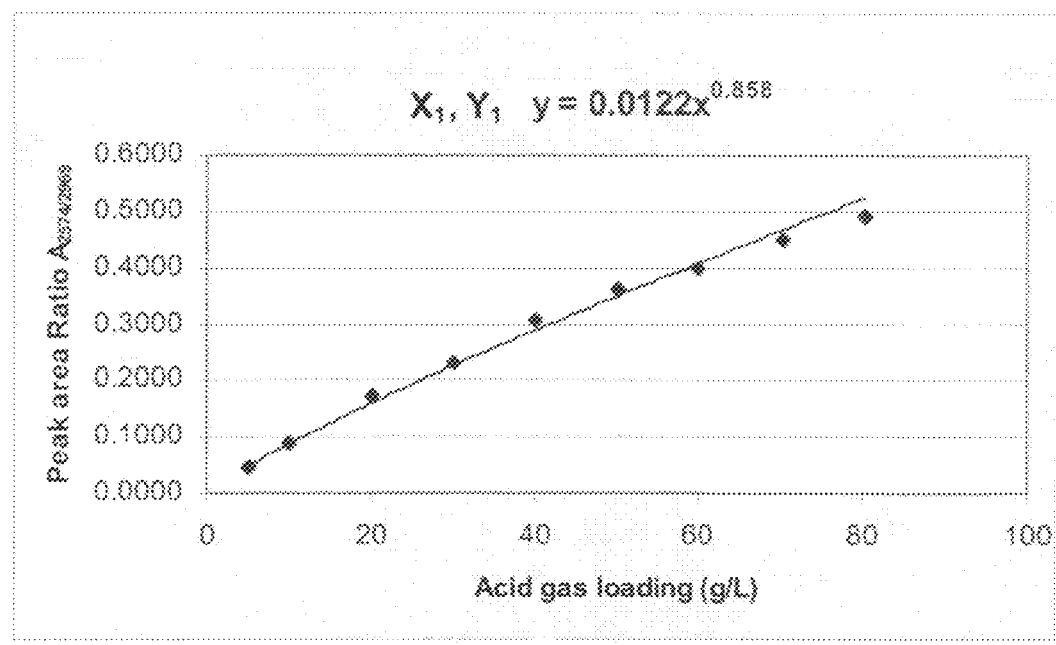
FIGS. 33A-E are correlation graphs of Raman peak ratios to acid gas loading.
Figure 33B:
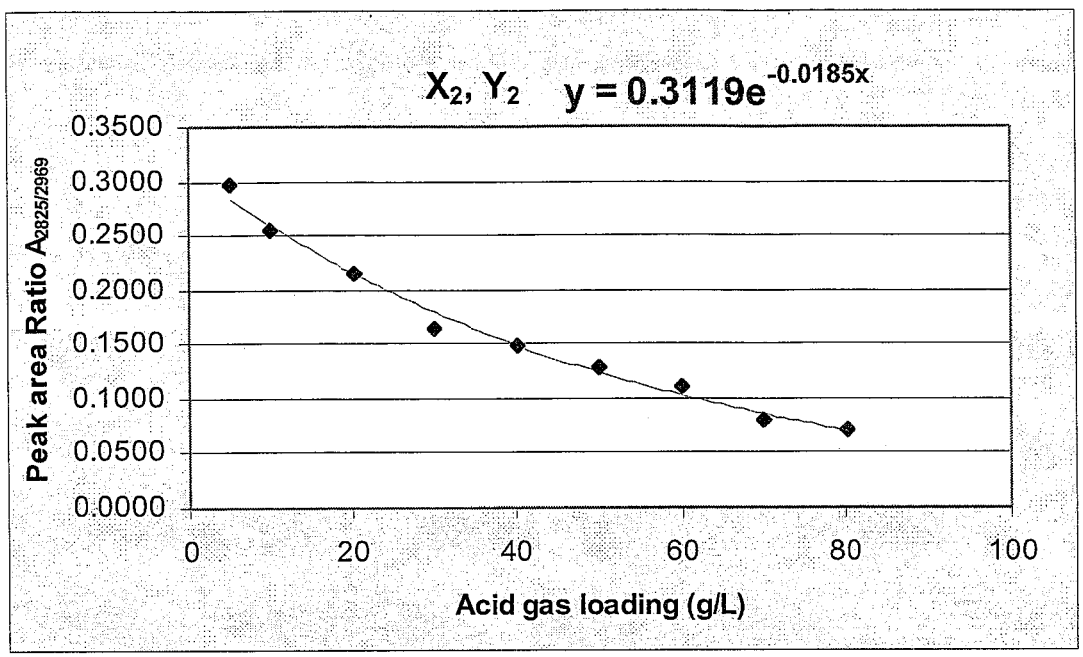
Figure 33C:
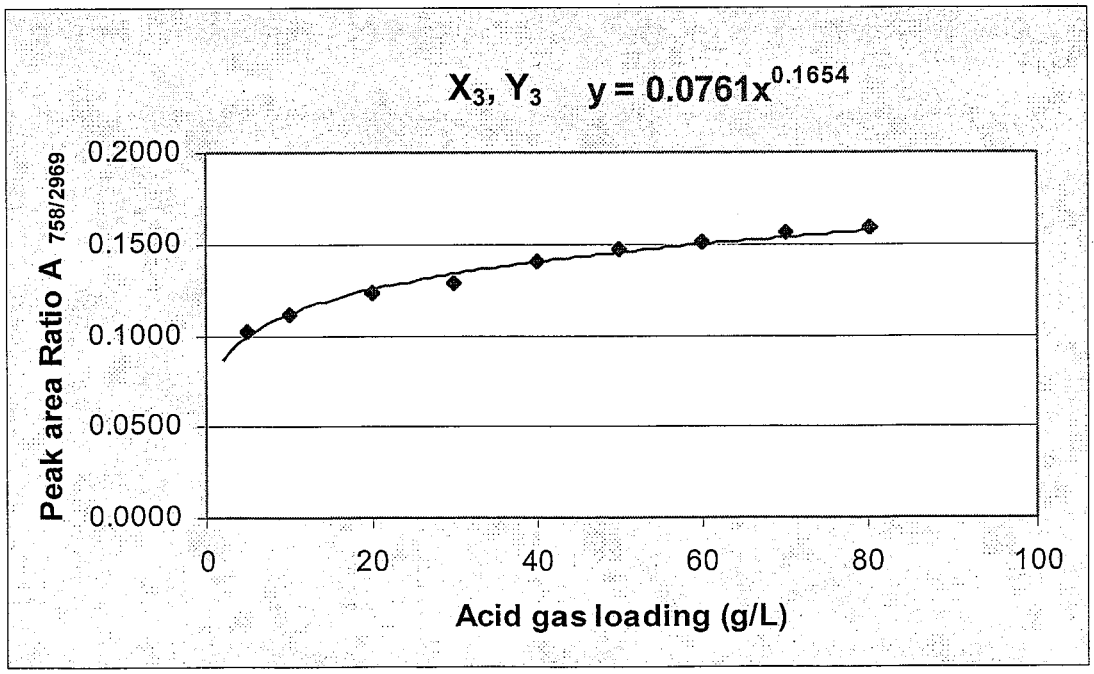
Figure 33D:
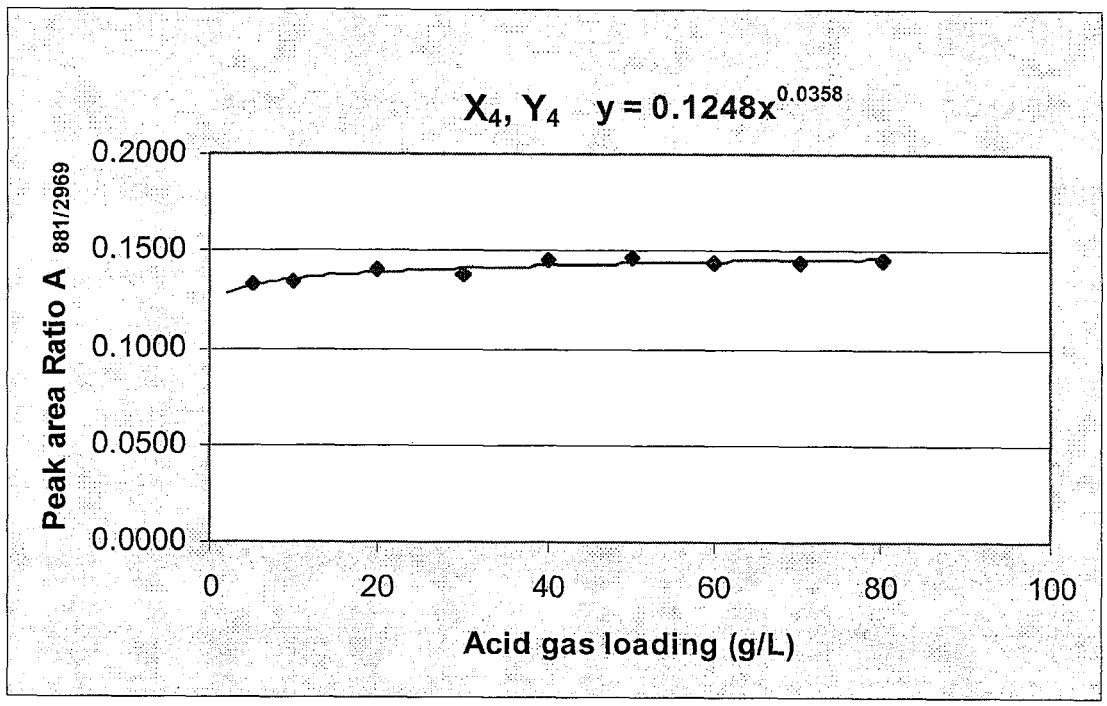
Figure 33E:
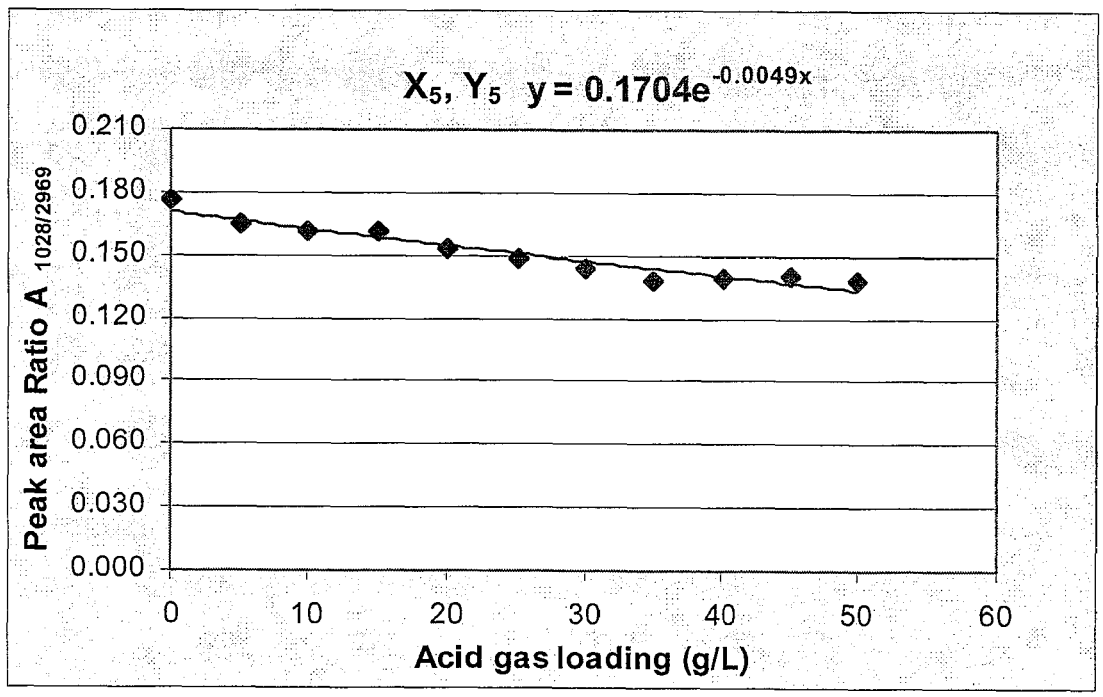
Figure 34A:
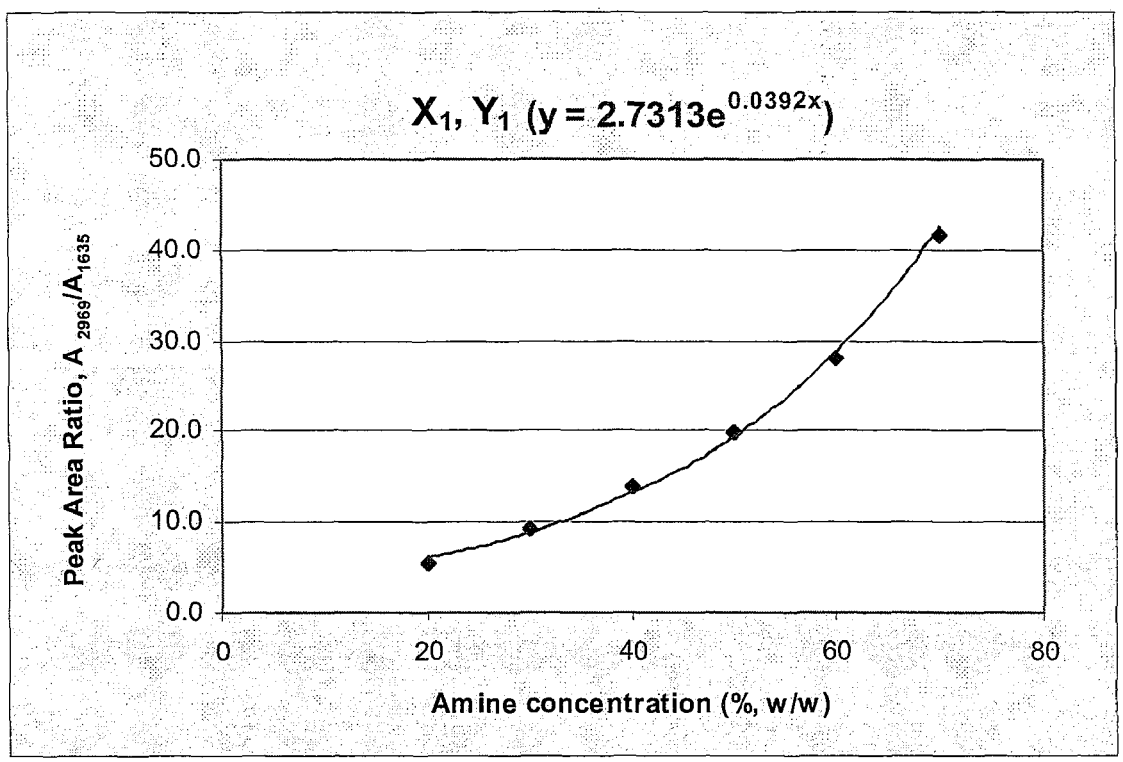
FIGS. 34A-C are correlation graphs of Raman peak ratios to amine concentration.
Figure 34B:
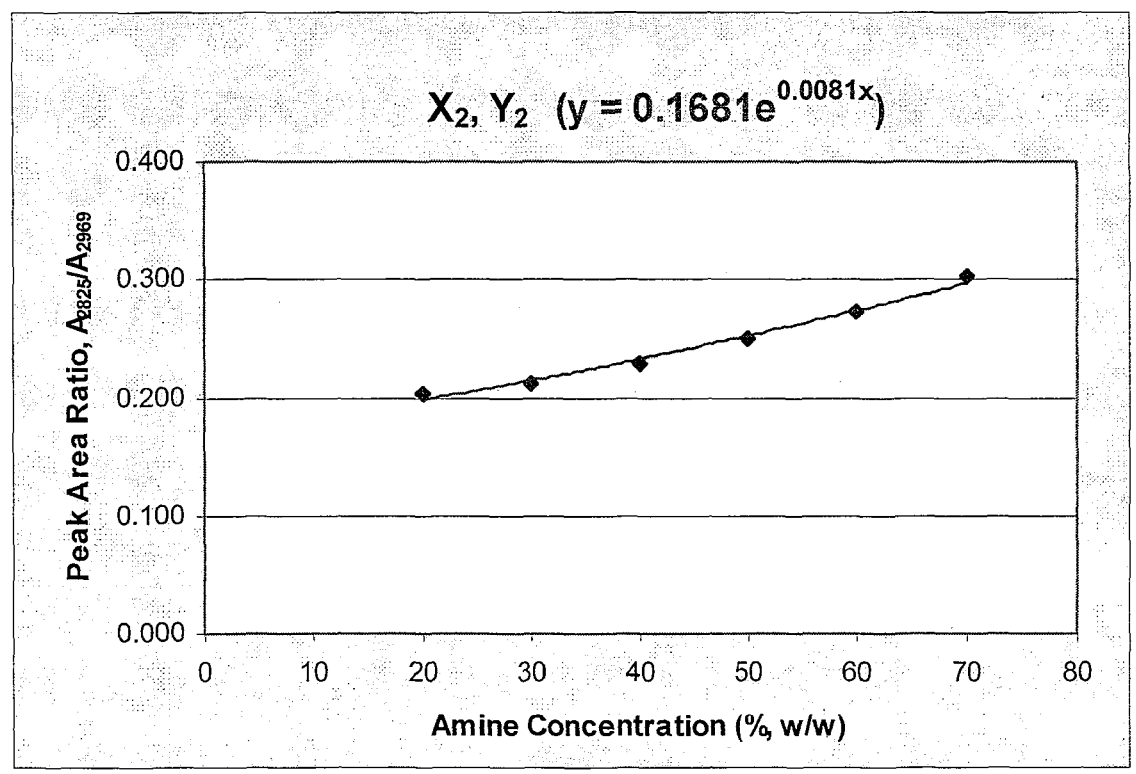
Figure 34C:
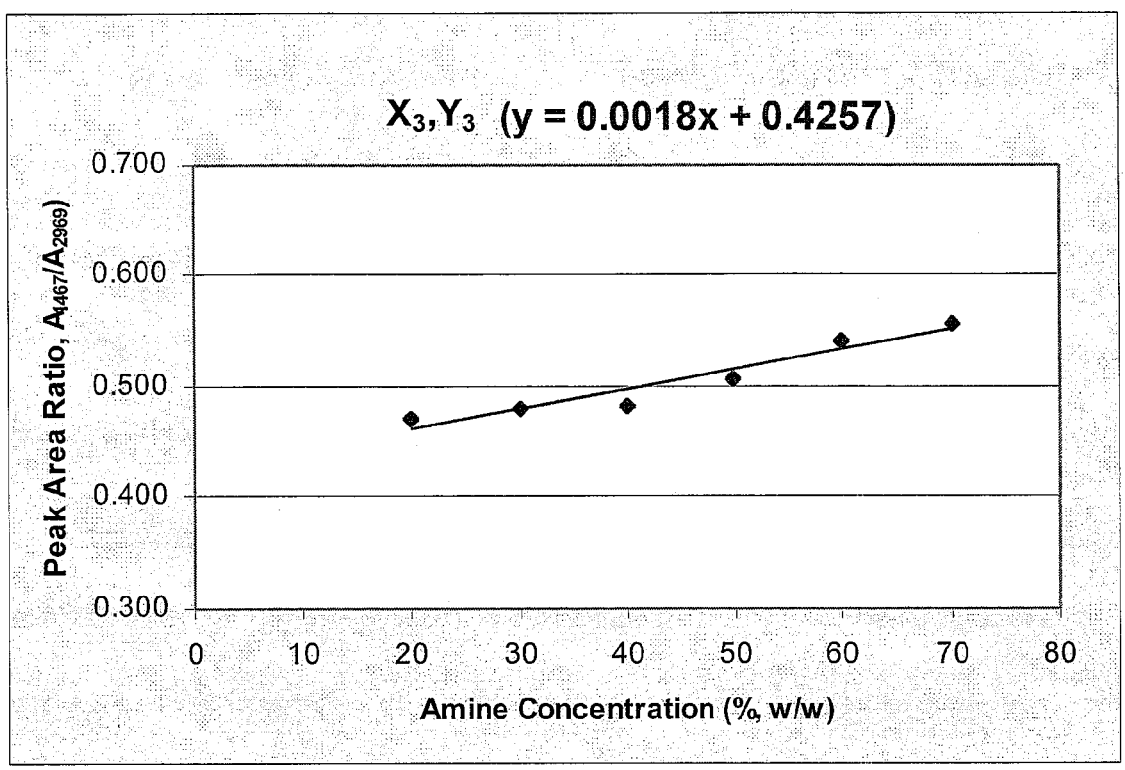

For inorganic based liquid absorption processes used to remove the acid components from the gas stream, such as the Benfield process and the Cat crab process, which are carbonate based liquid absorption processes, Raman spectra can be used to determine the acid components loading. In the Benfield process, potassium carbonate is used to absorb CO₂, H₂S and other acid components. When the acid components react with carbonate, bicarbonate is formed. In Raman spectra, carbonate and bicarbonate each have their own clear defined peaks at 1072 cm$^{-1}$ and 1020 cm$^{-1}$, respectively (FIG. 32). This peak intensity or peak area can be used to determine the CO₂ loading in the solution according to the basic absorption reaction:

$$K_2CO_3 + CO_2 + H_2O \rightarrow 2KHCO_3$$

$$CO_3^{-2} + CO_2 + H_2O \rightarrow 2HCO_3^-$$

$$OH^- + CO_2 \rightarrow HCO_3^-$$

$$H_2S + OH^- \rightarrow HS^-$$

The Raman spectra of carbonate and bicarbonate are very simple and clear. Unlike the spectra of amine solution, these spectra provide a clear window to detect other chemical components which absorb in the solution such as H₂S, and its signature peak at 2574 cm$^{-1}$.

Example 6

H₂S and CO₂ Concentration Calibration

Simulation tests were conducted by using the set up giving below. The purpose of the simulation tests were to calibrate the Raman results obtained in previous examples under the conditions of a rich amine stream in the field.

Figure 17A:
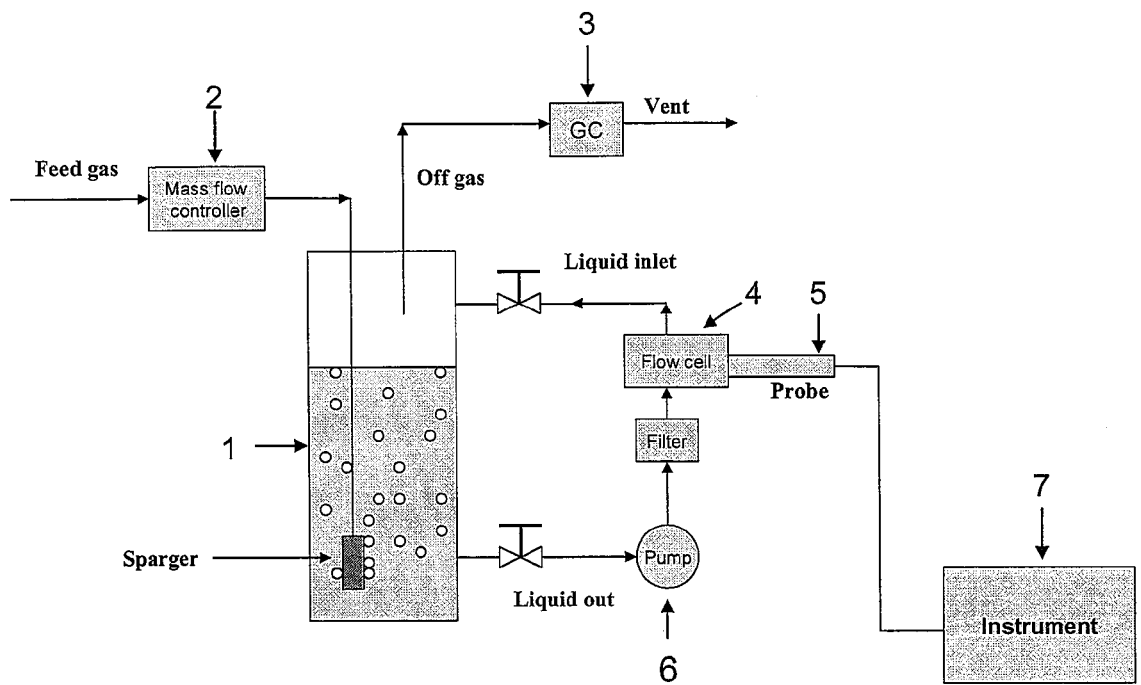
FIGS. 17A and 17B are schematic diagrams of the set up for $H_2S$ and $CO_2$ concentration calibration of rich amine stream at high pressure conditions.
Figure 17B:
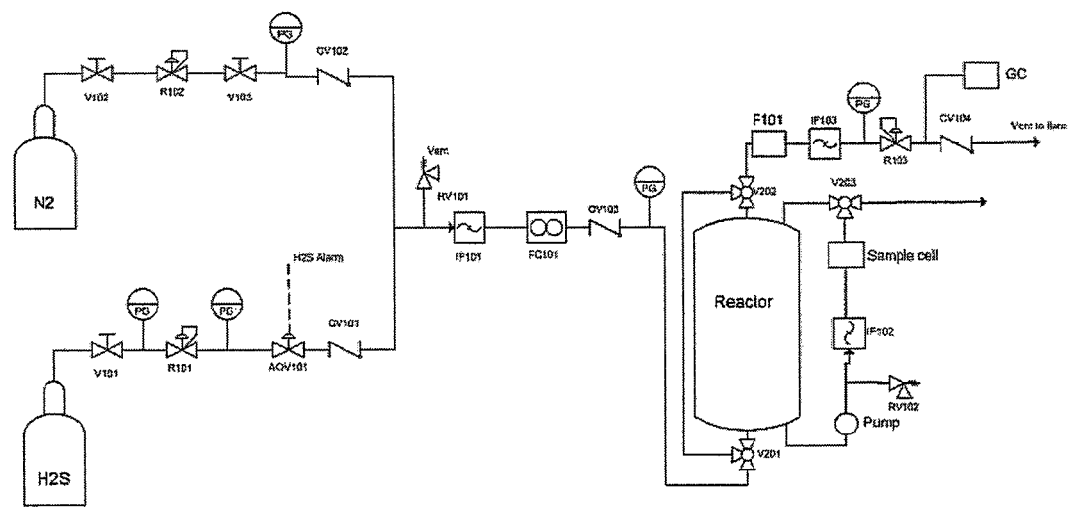

Sour gas service rated equipment was installed in the field. During normal operation, gas contained in the system has product gas vented to an enclosed flare vent system. A schematic representation of the test system is shown in FIG. 17A. A detailed flow sheet is shown in FIG. 17B.

The simulation consisted of a reaction vessel containing a sparger to disperse the gas stream containing CO₂ and/or H₂S under similar pressure to that of a rich amine stream in the field. The gas stream was monitored by a mass flow meter and controller which recorded and controlled the feed gas stream.

A gas chromatograph was used to record the off gas composition including unabsorbed sour gas, $CO_2$ and/or $H_2S$. The off gas not absorbed by the amine solution is vented into a contained vent system after the composition was determined by the gas chromatograph. The amount of sour gas absorbed in the liquid can be calculated using the feed gas composition, feed gas flow rate and the off gas composition recorded by the gas chromatograph.

The liquid loop of the simulation contained a pump to circulate the liquid through the system and also through the flow cell. To monitor the acid gas concentration in the liquid, a probe similar to that used in the previous examples was inserted into the flow cell to capture the signal to be sent to the Raman instrument.

The $CO_2$ loading and $H_2S$ loading simulated tests were conducted separately at a pressure of approximately 150 psi. The feed gas composition for the $CO_2$ loading simulation was 5 mol % $CO_2$ balanced with $N_2$. The feed gas composition for the $H_2S$ loading simulation test was 5 mol % $H_2S$ balanced with $N_2$.

The moles of acid gas loading in the liquid can then be calculated as the difference between the moles of acid gas in the feed gas and the moles of acid gas in the off gas. The moles of acid gas in the feed gas can be calculated by the composition of the feed gas and the flow rate whereas the moles of acid gas in the off gas can be calculated by gas chromatography.

Based on the ranking from the previous principal component analysis (PCA) on all 17 spectral components in Example 3, the spectral components, i.e. the peaks 2969, 2825, 2574, 1028, 881, 758 $cm^{-1}$ were found to be the most influential inputs. The peak area of these six most important spectral components were calculated and plotted against the loaded $CO_2$ or $H_2S$ concentrations, which were calculated by the amount difference of acid gas in the feed stream and off gas stream. The selected correlations of the loaded acid gas concentrations and the spectral components were given in FIG. 33 (A to E). The equations used to calculate the acid loading were extracted from the loaded acid gas concentration and the peak area ratio of the selected spectral components.

Therefore, the total acid loading in this case, including $CO_2$ and $H_2S$ loading, is given by the following equations:

$$X_{(total\ acid\ loading,\ g/L)} = AX^1 + BX_2 + CX_3 + DX_4 + EX_5$$

$$Y_1 = k_1 X_1^{b1} (Y_1 = A_{2574}/A_{2969},\ k_1 = 0.0122,\ b_1 = 0.8580)$$

$$Y_2 = k_2 e^{b2x2} (Y_2 = A_{2825}/A_{2969},\ k_2 = 0.3119,\ b_2 = -0.0185)$$

$$Y_3 = k_3 X_3^{b3} (Y_3 = A_{758}/A_{2969},\ k_3 = 0.0761,\ b_3 = 0.1654)$$

$$Y_4 = k_4 X_4^{b4} (Y_4 = A_{881}/A_{2969},\ k_4 = 0.1248,\ b_4 = 0.0358)$$

$$Y_5 = k_5 e^{b5x5} (Y_5 = A_{1028}/A_{2969},\ k_5 = 0.1704,\ b_5 = -0.0049)$$

A=0.4, B=0.2, C=0.2, D=0.1, E=0.1

Where, $H_2S$ loading = $X_1$ $CO_2$ loading = $X_{(total\ acid\ loading,\ g/L)} - X_1$ The factors, A, B, C, D and E are subject to change based on each spectral component's response weight. The factor k, and b, could also vary when the calibration need adjust for the lean amine stream, where the conventional chemical analysis methods are available to cross check the instrument calibrations.

Example 7

Amine Strength Calibration

The calibration of the amine concentration was conducted using the field test instrument of the previous example with the flow cell and the probe. Amine solutions of varying concentrations were made according to Table 8 and manually injected into the flow cell. The probe then gathered the spectral information of the amine solution and the spectrum was recorded by the Raman instrument.

TABLE 8

Amine Correlations using Spectral Peak Ratios from Simulation Tests

| Amine strength w/w % | Peak area ratio $A_{2969/1635}$ | Peak area ratio $A_{2825/2969}$ | Peak area ratio $A_{1467/2969}$ |
|---|---|---|---|
| 20 | 5.55 | 0.20 | 0.47 |
| 30 | 9.25 | 0.21 | 0.48 |
| 40 | 13.98 | 0.23 | 0.48 |
| 50 | 19.79 | 0.25 | 0.51 |
| 60 | 27.98 | 0.27 | 0.54 |
| 70 | 41.55 | 0.30 | 0.56 |

The amine strength was calculated by the equations below. The peak area of water at 1650 $cm^{-1}$ was used to ratio to the amine peak at 2969 $cm^{-1}$, which is $X_1$. The factors A, B, C are subjective to change depends on each spectral components response weight. The k and b values could also fine turned by the amine strength chemical analysis results.

$$X_{(amine\ strength,\ \%,\ w/w)} = AX_1 + BX_2 + CX_3$$

$$Y_1 = k_1 e^{b1 x1} (Y_1 = A_{2969}/A_{1635},\ k_1 = 2.7313,\ b_1 = 0.0392)$$

$$Y_2 = k_2 e^{b2 X_2} (Y_2 = A_{2835}/A_{2969},\ k_2 = 0.1681,\ b_2 = 0.0081)$$

$$Y_3 = k_3 X_3 + b_3 (Y_3 = A_{1467}/A_{2969},\ k_3 = 0.0018,\ b_3 = 0.4257)$$

A=0.7, B=0.2, C=0.1

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method of determining the concentration of an acid gas, comprising the steps of:
   (a) providing a sample of an amine or alkaline salt absorbing solution in which the acid gas comprising carbon dioxide or hydrogen sulphide is dissolved, and obtaining a Raman spectrum having characteristic peaks;
   (b) comparing the sample Raman spectrum to a baseline or control Raman spectrum and determining a spectral change of the amine or formed species comprising ionized amine, carbamate, hydrogen carbonate, carbonate, or hydrosulfide ion;
   (c) correlating the spectral change with the acid gas concentration.

2. The method of claim 1 wherein the amine comprises liquid amine, monoethanolamine, diethanolamine, methyl diethanolamine, diglycolamine, triethanolamine, or a diisopropanolamine.

3. The method of claim 1 wherein the alkaline salt solution comprises potassium carbonate solution, a caustic solution, a sodium carbonate solution, a sodium hydroxide solution or a potassium hydroxide solution.

4. The method of claim 1 wherein the spectral change comprises an increase or decrease in the peak height, or area under the peak, or both.

5. The method of claim 1 wherein the spectral change comprises a shift in a ratio of a first peak height or area to a second peak height or area.

6. The method of claim 1 wherein the spectral change occurs at about 2500 $cm^{-1}$.

7. The method of claim 5 wherein the first peak and second peak are selected from the group consisting of:

| First ($cm^{-1}$) | Second ($cm^{-1}$) |
|---|---|
| 300 | 1280 |
| 280 | 200 |
| 900 | 1000 |
| 400 | 1000. |

8. The method of claim 5 wherein the ratio is a ratio of peaks corresponding to ionized amine and free amine.

9. The method of claim 5 wherein one component of the ratio is a peak at 2969, 2825, 2574, 1028, 881, or 758 $cm^{-1}$.

10. A method of determining amine concentration of an amine solution, comprising the steps of:
    (a) providing a sample of the amine solution, and obtaining a Raman spectrum having characteristic peaks;
    (b) comparing the sample Raman spectrum to a baseline or control Raman spectrum and determining a spectral change of the amine;
    (c) correlating the spectral change with the amine concentration.

11. The method of claim 10 wherein the amine comprises monoethanolamine, diethanolamine, methyl diethanolamine, diglycolamine, triethanolamine, or a diisopropanolamine.

12. The method of claim 10 wherein the spectral change comprises an increase or decrease in the peak height, or area under the peak, or both.

13. The method of claim 10 wherein the spectral change comprises a shift in a ratio of a first peak height or area to a second peak height or area.

14. The method of claim 13 wherein the first peak and second peak are selected from the group consisting of:

| First ($cm^{-1}$) | Second ($cm^{-1}$) |
|---|---|
| 300 | 1280 |
| 280 | 200 |
| 900 | 1000 |
| 400 | 1000. |

15. The method of claim 13 wherein the spectral change comprises a change in the peak area ratio of a characteristic peak for the amine and a characteristic peak for water.

16. The method of claim 15 wherein the characteristic peak for the amine is about 2969 and the characteristic peak for water is about 1650.

17. The method of claim 15 wherein the amine comprises MDEA and the Raman peak intensity ratio comprises $1467_{(MDEA)}/1640_{(water)}$.

* * * * *